US008951960B2

(12) United States Patent
Wiatr et al.

(10) Patent No.: US 8,951,960 B2
(45) Date of Patent: Feb. 10, 2015

(54) SYNERGISTIC COMBINATION OF DBNPA AND POLYCYCLIC ANTIBACTERIAL PEPTIDE AS BIOCIDE IN BIOETHANOL PRODUCTION

(75) Inventors: Christopher L. Wiatr, Memphis, TN (US); Michael L. Corcoran, Memphis, TN (US); Thomas E. McNeel, Memphis, TN (US); Richard A. Clark, Memphis, TN (US); Rita de Cassia Bortoto Porto, Memphis, TN (US); David Oppong, Memphis, TN (US)

(73) Assignee: Buckman Laboratories International, Inc., Memphis, TN (US)

( * ) Notice: Subject to any disclaimer, the term of this patent is extended or adjusted under 35 U.S.C. 154(b) by 441 days.

(21) Appl. No.: 13/048,972

(22) Filed: Mar. 16, 2011

(65) Prior Publication Data
US 2011/0230394 A1   Sep. 22, 2011

Related U.S. Application Data

(60) Provisional application No. 61/315,607, filed on Mar. 19, 2010, provisional application No. 61/352,521, filed on Jun. 8, 2010, provisional application No. 61/365,658, filed on Jul. 19, 2010.

(51) Int. Cl.
| | |
|---|---|
| A23K 1/06 | (2006.01) |
| A01N 37/18 | (2006.01) |
| A01N 37/34 | (2006.01) |
| C12P 7/06 | (2006.01) |
| A01P 1/00 | (2006.01) |
| C07K 14/195 | (2006.01) |
| A23K 1/14 | (2006.01) |
| A01N 31/02 | (2006.01) |
| A01N 63/02 | (2006.01) |

(52) U.S. Cl.
CPC ............... *A23K 1/06* (2013.01); *C07K 14/195* (2013.01); *A23K 1/146* (2013.01); *A01N 31/02* (2013.01); *A01N 63/02* (2013.01); *C12P 7/06* (2013.01); *Y02E 50/17* (2013.01)
USPC .................. 514/2.4; 426/9; 426/31; 435/161

(58) Field of Classification Search
None
See application file for complete search history.

(56) References Cited

U.S. PATENT DOCUMENTS

| 1,323,540 A | 12/1919 | Moore |
| 2,802,774 A | 8/1957 | Griesbach |

(Continued)

FOREIGN PATENT DOCUMENTS

| EP | 0186498 | * 7/1986 | ............... C12H 1/00 |
| WO | 2007097874 A1 | 8/2007 | |

(Continued)

OTHER PUBLICATIONS

Bazzell et al., National Corn-to-Ethanol Research Center Laboratory Research Division, Jul. 16, 2009, seven pages.

(Continued)

*Primary Examiner* — Kevin S Orwig
(74) *Attorney, Agent, or Firm* — Kilyk & Bowersox, P.L.L.C.

(57) ABSTRACT

Methods for controlling the growth of bacteria in ethanol fermentation systems with antibiotic alternatives, which can be nonoxidizing biocides, stabilized oxidizers, or any combinations thereof, are described. As an option, a process or composition of the present invention can include one or more polycyclic antibacterial peptides. The methods can provide improvements, such as increased ethanol yields with minimal carryover of biocide into co-products of the processes.

22 Claims, 5 Drawing Sheets

(56) References Cited

U.S. PATENT DOCUMENTS

| | | |
|---|---|---|
| 3,642,580 A | 2/1972 | Ghose |
| 3,764,475 A | 10/1973 | Mandels et al. |
| 4,094,742 A | 6/1978 | Bellamy |
| 4,201,596 A | 5/1980 | Church et al. |
| 5,980,758 A | 11/1999 | LaZonby et al. |
| 2003/0228373 A1 | 12/2003 | Ludensky et al. |
| 2004/0035803 A1 | 2/2004 | Cronan, Jr. et al. |
| 2009/0233340 A1 | 9/2009 | Dailey et al. |
| 2010/0291649 A1 | 11/2010 | Solomon et al. |

FOREIGN PATENT DOCUMENTS

| | | | |
|---|---|---|---|
| WO | 2007149450 A2 | | 12/2007 |
| WO | 2009/001205 A2 | | 12/2008 |
| WO | WO 2009/010836 | * | 1/2009 |
| WO | 2011066318 A2 | | 6/2011 |

OTHER PUBLICATIONS

Voegele, "Is Recycling Yeast and Option?" Ethanol Producer Magazine, Oct. 2009, two pages.

International Search Report and Written Opinion issued in corresponding International Patent Application No. PCT/US2011/028587 dated Jan. 18, 2012 (13 pages).

Patent Examination Report No. 1 from the Australian Patent Office dated Mar. 21, 2013 received in corresponding Australian Patent Application No. 2011227374 (5 pages).

Ruckle et al., "Hop acids can efficiently replace antibiotics in ethanol production", International Sugar Journal (2006), vol. 108, pp. 139-147.

Henning et al., "New aspects for the application of nisin to food products based on its mode of action", International Journal of Food Microbiology (1986), vol. 3, pp. 135-141.

* cited by examiner

SYNERGISTIC COMBINATION OF DBNPA AND POLYCYCLIC ANTIBACTERIAL PEPTIDE AS BIOCIDE IN BIOETHANOL PRODUCTION

BACKGROUND OF THE INVENTION

This application claims the benefit under 35 U.S.C. §119 (e) of prior U.S. Provisional Patent Application No. 61/315,607, filed Mar. 19, 2010; prior U.S. Provisional Patent Application No. 61/352,521, filed Jun. 8, 2010; and prior U.S. Provisional Patent Application No. 61/365,658, filed Jul. 19, 2010; which are incorporated in their entirety by reference herein.

The present invention relates to processes to control the growth of bacteria in fermentation processes with antibiotic alternatives. More particularly, the present invention relates to processes for fermentation to produce ethanol with bacterial control using antibiotic alternatives which include at least one nonoxidizing biocide and/or at least one stabilized oxidizer.

Worldwide demand for industrial ethanol is increasing in view of its utility as a fuel or fuel supplement, e.g. in admixture with gasoline, and because of its availability from numerous renewable sources and waste materials.

Ethanol can be produced by fermentation using a wide variety of starch containing raw materials. Starch-based ethanol production generally includes preparing a mass of starchy feedstock that contains or can be degraded into fermentable sugars, adding water to make a mash, saccharification of cellulose or other complex carbohydrates into fermentable sugars, and adding yeast which ferments the sugar into ethanol and carbon dioxide. Ethanol is recovered by subjecting the fermented mash to distillation. A co-product of distillation in ethanol production is non-starchy solids containing proteins, fibers, and oils, which may be processed to produce "distillers dried grains with solubles" or "DDGS". DDGS are nutrient-rich and are commercially sold as an animal feed, feed supplement, or plant fertilizer.

A problem in the ethanol production industry is that ethanol fermentation process equipment and/or the mash can become contaminated with bacteria that reduce production yields. "Lactic acid bacteria" is one class of bacteria that poses a problem in this respect. Lactic acid bacteria include, for example, *Lactobacillus, Pediococcus, Leuconostoc* and *Weissella* species. Acetic acid bacteria, e.g., *Acetobacter* sp., can also cause problems by producing acetic acid or other organic acids which foul the process and reduce the yields of ethanol. Yeast converts sugars to ethanol, but bacteria also convert those same sugars to make lactic or acetic acid instead of ethanol, leading to reductions in ethanol production yield. To control the outbreak of such bacteria, antibiotics have been used in bioethanol fermentation processes. The antibiotics used for these treatments may include, for example, virginiamycin, penicillin, erythromycin, and tylosin. These antibiotics also are used in veterinary and human medicine. The risk of the bacteria developing drug-resistance to antibiotics from their use or overuse is a known and growing concern. Switching antibiotics or increasing antibiotic dosages may not provide a long-term solution and may compound the antibiotic resistance problem. Further, questions have been raised about non-specificity of the antibiotic to the target bacteria and fermentation products. Concerns also have been raised about the presence of antibiotic residues in the DDGS destined for animal feeds. Stricter legislative and regulatory controls on the use of antibiotics in ethanol fermentation applications may be enacted. Alternatives to antibiotics are needed for ethanol fermentation processes.

Chlorine dioxide (i.e., $ClO_2$) has been proposed as an oxidizing biocide. However, chlorine dioxide is a strong oxidizing agent which has nonselective antimicrobial action. Chlorine dioxide attacks both unwanted bacteria and yeast crucial to the fermentation process. Loss of yeast translates into loss of ethanol yield and/or a "sluggish" fermentation and/or a "stuck" fermentation. Chloride dioxide also generates chloride ions, which can corrode equipment and lead to iron deposits or pitting in the process equipment, as well as release iron and chromium into the process system, which can require costly repairs.

The present investigators have recognized a need for ethanol fermentation strategies that can displace antibiotics for bacterial control with minimal adverse environmental impact of their own.

SUMMARY OF THE INVENTION

A feature of this invention is to provide a method that uses antibiotic alternatives for control of bacteria in ethanol fermentation.

An additional feature of this invention is to provide a method that uses antibiotic alternatives for control of bacteria in processes used in ethanol fermentations, such as bacteria control in mash fermentations, beer wells, or combinations thereof.

Another feature of this invention is to provide a method that increases ethanol yield in ethanol fermentations using a non-antibiotic treatment having low or no adverse environmental impact.

An additional feature of the present invention is to provide a method that uses nonoxidizing biocides for control of bacteria in ethanol fermentations that are essentially absent from process end products.

Another feature of the present invention is to provide a method that uses stabilized oxidizers for control of bacteria in ethanol fermentations that are essentially absent from process end products and do not impair process equipment.

An additional feature of the present invention is to provide a method that introduces non-antibiotic biocides for control of bacteria in ethanol fermentations by adding the biocide to at least one post-fermentation source of process water which is recycled to the fermenter.

Another feature of the present invention is to provide antibiotic-free distillers dried grains products from bioethanol production with a method that uses non-antibiotic biocides for control of bacteria in ethanol fermentations, wherein the non-antibiotic biocides are essentially absent from the distillers dried grains products.

Additional features and advantages of the present invention will be set forth in part in the description which follows, and in part will be apparent from the description, or may be learned by practice of the present invention. The objectives and other advantages of the present invention will be realized and obtained by means of the elements and combinations particularly pointed out in the written description and appended claims.

To achieve these and other advantages and in accordance with the purposes of the present invention, as embodied and broadly described herein, the present invention, in part, relates to a method for producing ethanol by fermentation. The method includes fermenting a fermentable mash in the presence of at least one nonoxidizing biocide and yeast in a vessel to produce ethanol and a solids content, wherein the nonoxidizing biocide controls the growth of bacteria in the mash without reducing the yeast population. The method then involves distilling the fermented mash to separate at least a portion of the ethanol from the solids content. Ethanol yields can be increased by the present fermentation process without the need for antibiotics. Further, ethanol and distiller grain products of the fermentation process can be free or essentially free of the antibiotic alternative that is used. Acid content of the fermented mash can be reduced, reflecting that enhanced bacteria control is achieved.

The present invention also relates to a method of producing ethanol with fermentation that includes fermenting a fermentable mash in the presence of at least one stabilized oxidizer and yeast in a vessel to produce ethanol and a solids content, wherein the stabilized oxidizer controls growth of bacteria in the mash, and distilling the fermented mash to separate at least a portion of the ethanol from the solids content.

The present invention further provides a method for producing ethanol with fermentation that includes providing fermentable mash, non-antibiotic biocide, and yeast as a mixture in a vessel under conditions wherein fermentation of the mash occurs to produce ethanol and the biocide controls the growth of bacteria in the mash without reducing the population of the yeast, and distilling the fermented mash to separate at least a portion of ethanol from the solids content of the mash, wherein the non-antibiotic biocide is a nonoxidizing biocide, stabilized oxidizer, or combination thereof.

The present invention further provides a method for producing ethanol with fermentation that includes fermenting a fermentable mash in the presence of yeast in a vessel to produce ethanol and a solids content, storing at least a portion of the fermented mash in a beer well(s) in the presence of at least one nonoxidizing biocide wherein the nonoxidizing biocide controls the growth of bacteria in the beer well, and feeding stored mash from the beer well to a distillation unit, distilling the fermented mash in the distillation unit to separate at least a portion of the ethanol from the solids content. Nonoxidizing biocide can be added to both the fermentable mash in the fermentation vessel and the fermented mash in the beer well.

The present invention further provides a method for producing ethanol with fermentation that includes fermenting a fermentable mash in the presence of yeast and recycled process water in a fermenter vessel to produce fermented mash comprising ethanol and a solids content, optionally scrubbing gaseous emissions from the fermenter vessel with an aqueous solution and recycling at least a portion of the scrubber effluent solution into the fermenter vessel, optionally storing at least a portion of the fermented mash in a beer well, feeding fermented mash to a distillation unit, distilling the fermented mash in the distillation unit to separate at least a portion of the ethanol from stillage, separating the stillage into a liquids-containing fraction (thin stillage) and a solids-containing fraction, optionally recycling at least a portion of the thin stillage into the fermenter vessel, recovering the solids-containing fraction as at least in part wet distillers grains product and/or drying at least a portion of the solids-containing fraction to produce distillers dried grains product and evaporated vapors, and optionally condensing the evaporated vapors and recycling at least portion of the condensed vapors into the fermenter vessel, wherein a nonoxidizing biocide and/or stabilized oxidizer for control of bacteria in the fermenter vessel is added to (and/or present in) at least one source of recycled water comprising the scrubber effluent solution, the thin stillage, and the condensed vapors from grain drying, or any combinations thereof, before (re)introduction of the recycled water into the fermenter vessel.

The present invention further provides a method for producing distillers dried grains coproducts of ethanol production with fermentation that includes fermenting a fermentable mash in the presence of yeast in a fermenter vessel to produce fermented mash comprising ethanol and a solids content, optionally scrubbing gaseous emissions from the fermenter vessel with an aqueous solution and recycling at least a portion of the scrubber effluent solution into the fermenter vessel, optionally storing at least a portion of the fermented mash in a beer well, feeding fermented mash to a distillation unit, distilling the fermented mash in the distillation unit to separate at least a portion of the ethanol from stillage, separating the stillage into a liquids-containing fraction as thin stillage and a solids-containing fraction, optionally recycling at least a portion of the thin stillage into the fermenter vessel, recovering the solids-containing fraction with drying of at least a portion of the solids-containing fraction to produce distillers dried grains product and evaporated vapors, and optionally condensing the evaporated vapors and recycling at least a portion of the condensed vapors into the fermenter vessel, wherein nonoxidizing biocide and/or stabilized oxidizer for control of bacteria in the fermenter vessel is added to at least one of the fermenter vessel, beer well, and indicated recycled sources of water, or any combinations thereof. The distiller grains coproducts of the fermentation process can be free or essentially free of the antibiotic alternative that is used. The distiller grains coproducts can be free or essentially free of antibiotics without bacteria problems or other impairments when produced using methods of the present invention.

It is to be understood that both the foregoing general description and the following detailed description are exemplary and explanatory only and are only intended to provide a further explanation of the present invention, as claimed.

As used herein, "antibiotic" refers to a substance that controls the growth of bacteria, fungi, or similar microorganisms, wherein the substance can be a natural substance produced by bacteria or fungi, or a chemically/biochemically synthesized substance (which may be an analog of a natural substance), or a chemically modified form of a natural substance. The substance can be, for example, a compound.

"Fermentable sugar" refers to simple sugars such as monosaccharides and disaccharides (e.g., glucose (dextrose), fructose, galactose, sucrose, maltose) that can be used by yeast or other microorganisms in conversions to ethanol or other end products.

"Cellulosic material" refers to material containing cellulose. Cellulose is generally found, for example, in the stems, leaves, hulls, husks, and cobs of plants or leaves, branches, and wood of trees. The cellulosic material can be, but is not limited to, herbaceous material, agricultural residues, forestry residues, municipal solid wastes, waste paper, and pulp and paper mill residues. It is understood herein that the cellulose may be in the form of lignocellulose, a plant cell wall material containing lignin, cellulose, and hemicellulose in a mixed matrix.

"Biocide" refers to a chemical substance capable of controlling bacteria in a selective way.

"Nonoxidizing biocide" refers to a biocide that is selective to bacteria (i.e., attacks at least one bacterium but not yeast) in fermentation mash for at least one dosage.

"Controlling" the growth of at least one bacterium maintains the bacterial population at a desired level, reduces the population to a desired level (even to undetectable limits), and/or at least partially inhibits the growth of the bacteria. Further, it is also to be understood that "controlling" the growth of at least one bacterium can include biostatically reducing and/or maintaining a low level of at least one bacteria such that the reaction of the bacteria with sugars in a fermentation mash are mitigated, i.e., the bacterial growth rate or bacterial attack rate on fermentation sugars is slowed down and/or eliminated.

"Distillers Dried Grains" (DDG) refers generally to coproducts of ethanol production by fermentation which can comprise dried residual grain solids, which can be animal feed grade.

"Distillers Dried Grains with Solubles" (DDGS) refers to coproducts of ethanol production by fermentation which can comprise dried residual grain solids with solubles content, such as process syrup or other solubles, and which can be animal feed grade.

"Wet Distillers Grains" (WDG) refers to coproducts of ethanol production by fermentation which can comprise residual grain solids prior to drying, which can contain at least a portion of process syrup, and which can be animal feed grade.

The accompanying drawings, which are incorporated in and constitute a part of this application, illustrate some of the embodiments of the present invention and together with the description, serve to explain the principles of the present invention.

DETAILED DESCRIPTION OF THE PRESENT INVENTION

Figure 1:
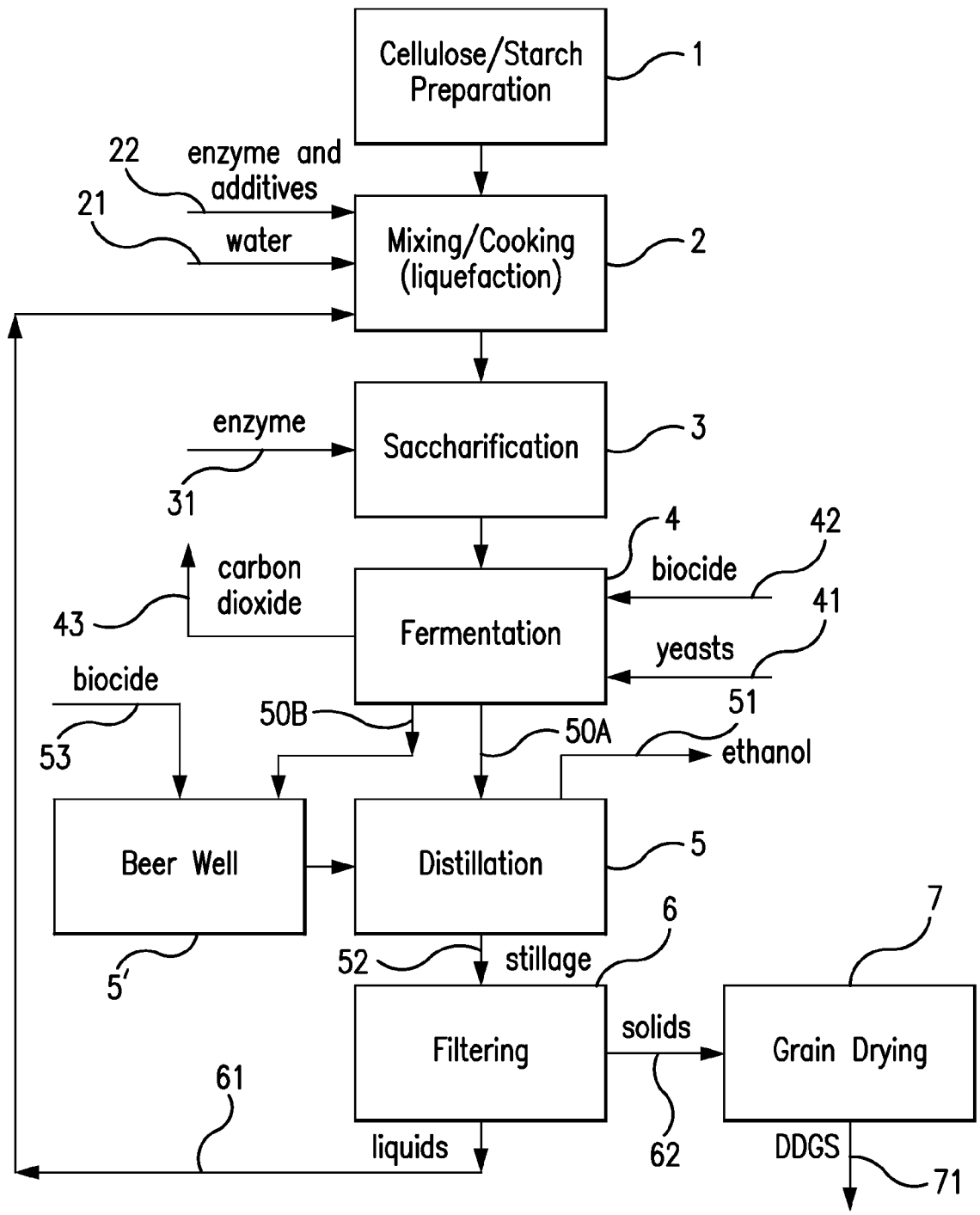
FIG. 1 illustrates a process flow diagram of a method of ethanol production with introduction of a non-antibiotic biocide for control of bacteria according to an embodiment of the present invention.

The present invention provides methods for controlling the growth of at least one bacterium in ethanol fermentation using at least one antibiotic alternative, for example, a non-antibiotic biocide, that can be absent or essentially absent from the process end products. The antibiotic alternative can be one or more nonoxidizing biocides, stabilized oxidizers, or any combinations thereof. These antibiotic alternatives are selective to bacteria relative to the fermentation yeasts, such that ethanol yields can be increased in the methods of the present invention, for example, increased at least about 0.5% by weight, or from about 0.5% to about 5% by weight, or from about 1% to about 3.5% by weight, or from about 1.25% to about 2.5% by weight, as compared to the same fermentation process without the antibiotic alternative. In industrial scale production, even seemingly small increases in yields can be significant. Also, the distillers dried grains (DDG), such as distillers dried grains with solubles (DDGS), produced from the methods of the present invention can be antibiotic-free. Further, the antibiotic alternatives can degrade or react to form other materials having lower if any environmental impact during fermentation processing and before ethanol and DDG (e.g., DDGS) recoveries. The antibiotic alternative used in the methods of the present invention, i.e., the nonoxidizing biocide or stabilized oxidizer, is not believed to survive the process into the DDG, such as DDGS (e.g., the biocide breaks down and/or otherwise is not present). Therefore, the non-antibiotic biocide is not expected to end up in animal feed having the DDG (e.g., DDGS), and not in subsequent end products, such as marketed meats, obtained from the livestock, poultry, or fish fed the DDG (e.g., DDGS). The DDG and DDGS co-products of the fermentation process, for example, can be free or essentially free of the nonoxidizing biocide or stabilized oxidizer used to control bacteria during fermentation. For example, DDG coproducts, such as DDGS coproducts, of methods of the present invention can contain the antibiotic alternatives used in fermentation methods of the present invention in an amount of less than about 100 ppm, less than about 10 ppm, or less than about 5 ppm, or less than about 1 ppm, or less than detectible amounts (e.g., 0.01 ppm to 10 ppm, 0.0001 ppm to 5 ppm, 0.001 ppm to 1 ppm).

The present invention also provides methods for introduction of non-antibiotic biocides for control of bacteria in ethanol fermentations by adding the biocide to at least one post-fermentation source of process water which is recycled to a fermenter. The treatment of post-fermentation sources of water with the indicated non-antibiotic biocides before these water sources are recycled to the fermenter can provide control of bacteria which may have contaminated the water source during fermentation or post-fermentation processing. Treatment of the recycled water with the indicated biocides to control bacteria therein before (re)introduction to the fermenter can prevent or reduce the risk of infections of the fermenter or other process units by the recycled water.

In general, the processes for converting a complex carbohydrate or starch to fermentable sugar usually include a number of steps. In a typical process such as used for grains and cereals containing granular starch, for example, two processes of milling are generally used, which are referred to in the art as wet milling and dry milling. Milled starch-containing material is then mixed with an aqueous solution to produce a slurry. In a dry milling process, the aqueous solution that is mixed with the milled starch-containing material typically includes not only water but also varying amounts of thin stillage and/or other recycled sources of water in the process system. The thin stillage and/or other recycled sources of water can be used to conserve water usage in fermentable sugar and/or alcohol processing. The starch is then converted to short chain less viscous dextrins by a liquefaction process, which generally involves gelatinization of the starch simultaneously with, or followed by, addition of a suitable enzyme for that purpose. The liquefied starch is then converted to low molecular weight sugars by a saccharification step, which typically includes enzymatically using another suitable enzyme. The low molecule weight sugars may be further purified (e.g. to purified dextrose), and metabolized by a fermenting microorganism, such as yeast, to ethanol. As indicated, the saccharification and fermentation steps may be carried out sequentially or simultaneously. The resulting fermented mass can be distilled to separate ethanol product from stillage, which can be further processed to form distillers dried grains coproduct(s).

*Lactobacillus* species, such as *Lactobacillus plantarum*, are often a problem in ethanol fermenters. Other bacteria can attack substrates in the fermenters; for example, obligate anaerobes, such as acetic acid bacteria. Conditions become anaerobic in the fermentation process from insufficient oxygen concentration, encouraging acetic acid bacteria (e.g., *Acetobacter*) to grow and outcompete aerobic bacteria for nutrients, and overgrow them, producing acetic acid by catabolism. The acetic acid produced can be another problem in ethanol fermentation. The yeast can be approximately ten times more sensitive to acetic acid than the lactobacilli. Therefore, ethanol fermentation using yeast is negatively affected by the acetic acid bacteria, as well as lactobacilli. Acetic acid can cause foul ferment at a beer well of a distillation unit. A beer well is a feedstock reservoir of fermented mash for a distillation unit. In the present invention, one or more nonoxidizing biocides and/or stabilized oxidizers are used in the methods of the present invention to selectively control lactobacilli, acetic acid bacteria, and/or other bacteria that would reduce ethanol yields or otherwise impair the fermentation process, and not the beneficial yeast. Thus, the use of antibiotic alternatives such as nonoxidizing biocides or stabilized oxidizers in the present methods for controlling the bacteria but not harming the yeast, allows the yeast to appropriately ferment unimpeded by the presence or growth of bacteria, particularly the bacteria which grow anaerobically and/or form acetic acid harmful to the process(ing) (e.g., the biocide does not reduce or kill yeast). The target bacteria can be, for example, a *Lactobacillus* species, an obligate anaerobe, or any combinations thereof. The fermented mash can have at least about 5-fold (5×), or at least about 10-fold (10×), or at least about 25-fold (25×), less lactic acid, or acetic acid, or both, on a weight % basis than the same fermented mash processed in the absence of the nonoxidizing biocide or stabilized oxidizer, which reflects the enhanced bacteria control achieved in methods of the present invention. Ethanol yields are enhanced and product quality, especially with respect to the DDGS, is free or essentially free of antibiotics and biocides that may be unwanted in the environment or food chain. For purposes of the present invention, it is to be understood "without reducing yeast population" means no significant reduction in the yeast population (e.g., less than a 10% reduction in the yeast population within 30 minutes of introducing the biocide).

FIG. 1 shows a flow chart illustrating a non-limiting method of the present invention. Starch-based ethanol production of processes of the present invention generally includes process steps or operations of preparing the raw cellulose or starchy material (e.g., milling) (1), mixing/cooking (liquefaction) (2), saccharification (3), fermentation (4) in the presence of the oxidizing biocide or stabilized oxidizer, optional beer well storage (5') with oxidizing biocide or stabilized oxidizer treatment, distillation (5) to produce ethanol product, filtration of stillage (6), and grain drying (7) to recover DDGS co-product. Depending on the type of feedstock, the feedstock material may be subjected to one or more prior unit operations such as milling, cutting, screening, and/or other methods to make the material easier to process and make material surfaces more accessible to treatment agents, indicated generally as step 1 in the figure. The prepared feedstock material (e.g., comminuted feedstock) can be mixed with water (21) and a solubilizing agent (22), and cooked, indicated as step 2. In step 2, "liquefaction" refers to a process of solubilizing and hydrolyzing cellulose or other complex carbohydrates in the feedstock. A suitable heat-stable solubilizing enzyme or acid can be used to hydrolyze the raw starch material, providing a liquefied mash. Other additives, such as pH adjusting agents, may be added in step 2. In step 3, a saccharifying agent (31), such as a saccharifying enzyme, can be added to the product of step 2 to convert the liquefied mash to fermentable sugars (e.g., fermentable monosaccharides). The fermentable sugars can be metabolized by a fermenting organism, such as, yeast. As indicated, multiple enzyme treatments may be needed to convert the starting cellulose or complex carbohydrate to a less complex starch, and ultimately into a fermentable sugar. Yeast (41) and biocide (nonoxidizing biocide or stabilized oxidizer) (42) can be added to the mash in a fermentation vessel, indicated as step 4, which ferments the sugar into ethanol and carbon dioxide (43). Yeasts grown in seed tanks (not shown), for example, can be added to the mash to begin the process of converting fermentable sugars to ethanol. The nonoxidizing biocide and/or stabilized oxidizer can be added to the mash to control any problematic bacteria present during fermentation. As understood in the fermentation industry, the liquefaction and/or saccharification steps can be carried out simultaneously with, or separately from, the fermentation step. For example, the saccharification and yeast fermentation processes may be performed in separate process zones, or simultaneously, at least in part, in the fermentation zone. Saccharification, for example, can occur while the mash is filling the fermentor in preparation for the fermentation step, although not limited thereto. As also understood in the industry, saccharification reactions may necessarily occur before yeast fermentation reactions can occur, where the respective saccharifying agent and yeast are present with mash in the same fermentation vessel.

As indicated by process path 50A, the fermented mash can be conducted directly from the fermentation vessel to a distillation column or other distillation unit. As indicated by process path 50B, the fermented mash can be stored in a beer well(s), indicated in step 5', before the mash is conducted to a distillation column or other distillation unit. The beer well can store the fermented beer between batches and can supply a continuous stream of fermented mash to the ethanol recovery operations, including distillation. One or both of process flow paths 50A and 50B for the fermented mashes can be used. Biocide (nonoxidizing biocide or stabilized oxidizer) (53) can be added to the fermented mash in the beer well to control any problematic bacteria present in the beer well. A single beer well or plurality of beer wells may be used and treated with biocide. Ethanol (51) generated by the fermentation reaction is recovered by subjecting the fermented mash to distillation, indicated in step 5. Depending on the type of distillation, the ethanol stream (51) may be sieved or otherwise further processed (not shown) to separate out water content and further purify the recovered ethanol product. The stillage (52) co-product of distillation in ethanol production contains non-starchy solids containing proteins, fibers, and oils, which can be processed to produce the DDGS that can be antibiotic-free and free or essentially free of the nonoxidizing biocide or stabilized oxidizer. This stillage (52) can be referred to as "whole stillage" where it is solids containing material remaining after fermentation and initial distillation of the alcohol ("beer column bottoms"). As illustrated, the stillage (52) can be filtered, as indicated in step 6, to separate liquids (61), such as thin stillage, that can be reused in the process from solids (52) that can be dried, as indicated in step 7, to produce DDGS (71). The stillage can be, for example, centrifuged, pressed, sieve or mesh filtered, or otherwise processed to separate liquid and solid fractions in separation step 6.

For purposes of the present invention, the nonoxidizing biocide and/or stabilized oxidizer can be introduced before and/or during fermentation. The biocide can be introduced in any manner, as a solid or liquid or even gas. The biocide can be introduced continuously or as a batch. The biocide can be introduced before and/or during fermentation. The biocide can even be applied to the vessel (e.g., to the walls of the vessel) prior to the mash being introduced into the fermentation vessel. The biocide is preferably introduced at least just prior to adding the yeast and/or at about the same time (or right after) the yeast is added (e.g., within 6 hours, within 3 hours, within 1 hour, within 30 minutes, within 10 minutes of adding the yeast). The biocide can be introduced into the fermentation vessel, and/or a line going into the fermentation vessel, and/or a vessel upstream of the fermentation vessel (e.g., saccharification vessel), and/or a source or sources of water recycled directly into or indirectly into (e.g., upstream of) the fermentation vessel. The biocide can be introduced as a single batch, multiple batches, as a drip line, and the like.

As indicated, the biocide (nonoxidizing biocide or stabilized oxidizer) can be added in a beer well(s), if used, which stores fermented mash. The biocide can be introduced before and/or during and/or after introduction of the mash to the beer well, and/or in a line going into the beer well, such as a line feeding mash to the beer well. The biocide can be introduced continuously or as a batch to the beer well. The biocide can be applied to the beer well (e.g., to the walls of the beer well) prior to the fermented mash being introduced into the beer well. The biocide can be introduced at the beer well as a single batch, multiple batches, as a drip line, and the like. The biocide can be added before, during and/or after any other processes in the ethanol production to control problematic bacteria.

Figure 2:
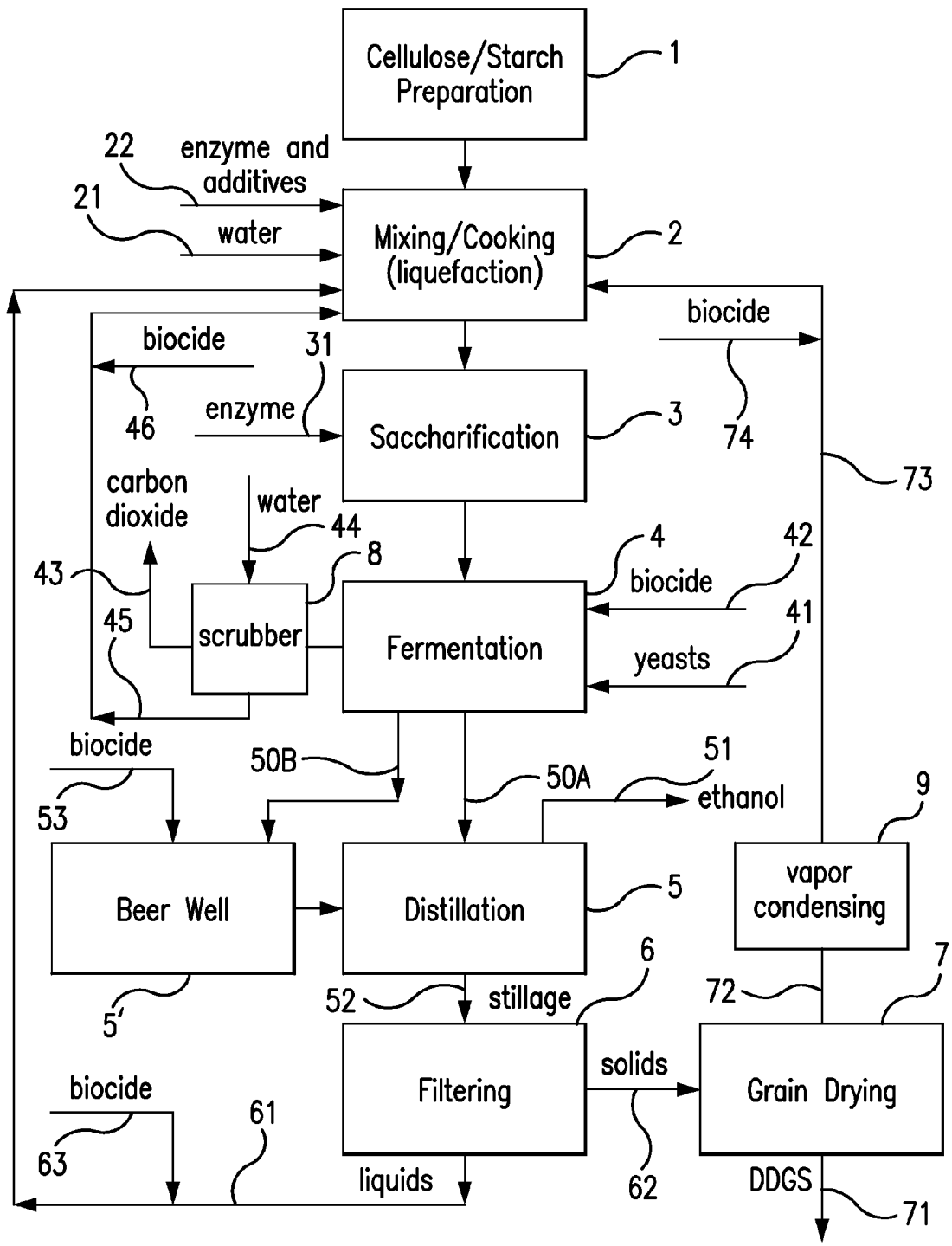
FIG. 2 illustrates another process flow diagram of a method of ethanol production in a production plant with introduction of a non-antibiotic biocide for control of bacteria according to an embodiment of the present invention.

FIG. 2 shows a flow chart illustrating a non-limiting method of the present invention where biocide addition can be made in at least one source of process water recycled into the fermentation vessel. The process flow and layout of process units in FIG. 2 is substantially similar to that of FIG. 1, and reference is made thereto with respect to similarly numbered elements and units which can have substantially similar meaning as shown for FIG. 1. For water conservation and/or other purposes, different post-fermentation sources of water can be recycled to an entry point or points upstream of the fermenter (e.g., at stages 1, 2 and/or 3), and/or directly into the fermenter or fermenters used for the fermentation (4). For example, thin stillage (61) can be recycled to the fermenter(s) used for fermentation. The thin stillage can be recycled to an introduction point or points upstream of the fermenter(s), such as illustrated in a non-limiting manner in FIG. 2, or directly therein. From about 10% to about 90%, or from about 25% to about 75%, or from about 40% to about 60%, or about 50%, for example, or other volumetric amounts of the thin stillage may be recycled for use in preparing a corn slurry. The relative amount may differ between different plants and operations, and may be changed over time, for example, to maintain water and solids balances. As described infra, for example, any non-recycled portions of the thin stillage may have other processing applied, such as evaporation in making process syrup which can be added to the solids before or after drying in producing DDGS coproduct. The water in the beer well, distillation column, or both can be contaminated with bacteria, e.g., acetic acid bacteria, which if left untreated with biocide before recycled, such as recycled thin stillage, could lead to a situation of filling the fermenter(s) with contaminated water and risking (re)infecting the fermentation operations to pretreatment or non-treatment conditions. To eliminate or at least reduce this risk, the thin stillage, in one option, can be treated with biocide (63) in return stream (61) before re-introduction into the process system upstream of or at the fermenter(s), or at other process locations. Typically, not all water or other volatile liquids carried over with solids (62) that goes to DDGS (71) via the grain drying step (7) is lost from the system. A predominant portion, e.g. about 80% or more or other percentages, of water in solids (62) can be recovered as condensate from the evaporator (dryer) and returned to the slurry system as recycled water. A vapor stream (72) produced from the drying step (7) can be cooled in a vapor condensing step (9) to provide a condensed vapor stream (73), which also can be recycled and used as a source of process water fed to the fermenter(s). In another option, the condensed vapor stream (73) can be treated with biocide (74) before re-introduction into the process system upstream of or at the fermenter(s), or at other process locations. As a large proportion of water content of the stillage can be returned to the slurry system in one form or another, such as, for example, from about 50% to about 95% by volume, or from about 75% to about 92% by volume, or about 90% by volume, or other percentages, the treatment of these recycled sources of process water with the indicated biocides can provide an effective approach to prevent or reduce risk of bacterial infection and/or growth problems in the fermenter, beer well, or other process units or lines. Another water input option to the slurry system fed to the fermenter(s) or fermenter(s) directly can be scrubber water. As yeast ferment the sugar, carbon dioxide gas (43) can be released with other fermentation gases such as volatile organic compounds and water vapor. The carbon dioxide can be released directly to the atmosphere or, as shown, can be purified with a scrubber in a scrubbing step (8) before released. The scrubbing step can be used to remove volatile organic compounds (including, e.g., ethanol) from the fermentation gases containing carbon dioxide. Water (44) is fed through a scrubber in scrubbing step (8) and contacts the fermentation gases to remove pollutants and to recover ethanol that would otherwise be lost due to evaporation from the fermenter. The aqueous effluent (45) from the scrubbing step also can be recycled as a source of process water for fermentation. As another option, the scrubber effluent (45) can be treated with biocide (46) before re-introduction into the process system upstream of or at the fermenter(s), or at other process locations. Any additional sources of water that may be desired or used for water requirements of the fermentation process or other processing can come, for example, directly from the plant's water supply (e.g., municipal water, wells, etc.), which amounts may be a relatively small amount or otherwise. These other potential sources of water for the system may not need treatment with the biocide, although such treatment can be applied if desired or needed.

With the present invention, the bacteria levels (e.g., lactic acid bacteria) (e.g., in the mash, fermented mash, or recovered ethanol or recovered DDGS or water sources recycled into the fermenter) during and/or after fermentation which can be treated with the nonoxidizing biocide and/or stabilized oxidizer can be below about $10^9$ CFU/ml (Colony Forming Units per ml), or below about $10^8$ CFU/ml, or below about $10^7$ CFU/ml, or below about $10^6$ CFU/ml, or below about $10^4$ CFU/ml, or from about 1 CFU/ml to about $10^9$ CFU/ml, or from about 10 CFU/ml to about $10^8$ CFU/ml, or from about $10^2$ CFU/ml to about $10^7$ CFU/ml, or from about $10^3$ CFU/ml to about $10^6$ CFU/ml, or other levels.

It will be understood that the use of the nonoxidizing biocide and/or stabilized oxidizer in methods of the present invention encompasses ethanol production using any feedstock material containing a source of fermentable sugar. The feedstock material can be any variety of carbohydrate which can be broken down by microbial fermentation. For example, the feedstock material for the method of the present invention can be any carbohydrate or starch material that is a source of fermentable sugar, either as a direct source of fermentable sugar, or as a material which can provide fermentable sugar by degradation or conversion of the original or an intermediate starch, cellulose, or polysaccharide component thereof. Examples of suitable sources of feedstock materials are agricultural crops, such as grains (e.g., corn, wheat, grain sorghum (milo)), barley, rice, rye, sugar cane, sugar beets, fodder beets, molasses, potatoes, carrots, cassava, rhubarb, parsnips, and sweet sorghum. Agricultural waste associated with crops may be used. Ethanol can be produced by fermentation with methods of the present invention using other starchy feedstock materials such as biomass, for example, such as wood chips, sawdust, switchgrass (*Panicum virgatum*), corn stover, corn cobs, straw, grain hulls, as well as recycled paper and waste paper materials and products, or any combinations thereof. The biomass material may be lignocellulosic biomass material, such as woody materials, or it may be a grassy material, such as switchgrass, that is low in lignin. Additional feedstock materials can include fruits and/or fruit juices (e.g., grapes, plums, berries, apples, pears, cherries), cattails, refined sugar (e.g., sucrose), honey, tree sap (maple, palm), flowers (dandelion, hibiscus), or any combinations thereof. It is understood in the industry that these and/or other different feedstocks for ethanol fermentation may have different ethanol yields, such as due to different starch contents and compositions, and different co-products. As indicated, it is believed that the methods of the present invention using the nonoxidizing biocides and/or stabilized oxidizers for bacteria control in ethanol production can be used without limitation with respect to the starchy feedstock.

Where cellulose-containing feedstock or other complex carbohydrate-containing feedstocks are used that are not directly fermentable sugars, several reactions typically are used to convert the complex carbohydrate to ethanol. As indicated, "liquefaction" and "saccharification" are usually used in conjunction with "fermentation," where a feedstock for ethanol production is used that contains a complex carbohydrate that is not a directly fermentable sugar with yeast, but can be degraded to release or provide fermentable sugars.

Liquefaction and saccharification may be performed with enzymes or acids. The first reaction can be, for example, an enzymatic or acidic hydrolysis of cellulose or other complex carbohydrate into fermentable sugars or smaller precursors thereof. Enzymatic hydrolysis, for example, may lead to intermediate saccharides requiring further enzymatic catalysis to achieve fermentable sugars. Saccharification by addition of acids, such as dilute mineral acids, is described, for example, in U.S. Pat. Nos. 1,323,540 and 4,201,596, which are incorporated herein in their entireties by reference. Saccharification by enzyme catalyzed hydrolysis, such as using cellulytic enzymes or cellulases, for example, for cellulose-containing feedstocks, are described, for example, in the U.S. Pat. Nos. 3,764,475 and 3,642,580, which are all incorporated herein in their entireties by reference. Additional microbial or enzymatic agents for inducing microbiological saccharification of cellulose can include, for example, or *Aspergillus niger* mutant 817, and thermophilic cellulolytic sporocytophaga, as described in the U.S. Pat. No. 4,094,742, which is incorporated herein in its entirety by reference. With corn, for example, the starches usually are broken down into dextrins and dextroses with enzymes before fermentation. Liquefaction and saccharification, respectively, of corn, for example, can be done in stages with alpha-amylase enzyme, for example, used to break down the corn starch into short chain dextrins, and glucoamylase enzyme, for example, can be used to break down the dextrins to form fermentable sugars. Wheat ethanol production is not significantly different from corn ethanol production and can be used instead of corn with minor operational adjustments known and used in the industry. Also, wheat has a higher protein content than corn, but slightly lower starch content, more fiber and pentosans, which are hemicelluloses that are high in viscosity and harder to break down into starch. Because of the lower starch content, wheat generally will produce less ethanol but more distillers grains than corn. The fiber portion of the sugar cane (e.g., bagasse) can be enzymatically treated to degrade the cellulose to fermentable sugars. Sugar cane juices (and some fruit juices) may be suitable for direct fermentation. Many tradeoffs in terms of ethanol yields and types of coproducts, as well as process ease, based on the type of feedstock selected and used, are generally known by those skilled in the fermentation industry. The use of the nonoxidizing biocide or stabilized oxidizer for control of bacteria during fermentation in the method of the present invention can be adapted to various possibilities and options in this respect. The amount of each enzyme (e.g., cellulytic enzyme(s)) added for saccharification of cellulosic material can be, for example, about 0.001% to about 2% by weight enzyme, or from about 0.01% to about 1% by weight enzyme, or from about 0.015% to about 0.5% by weight enzyme, or from about 0.2% to about 0.75% by weight enzyme, or from about 0.1% by weight to about 0.5% by weight enzyme, or from about 0.2 to about 0.4% by weight enzyme, based on fermentable material on solids weight basis, though other amounts may be used. The amount of solubilizing enzyme added for a liquefaction step can be in similar range amounts. Any amounts of enzyme indicated herein can be based on active enzyme.

Fermentation can involve the conversion of the fermentable sugars to ethanol, and this is usually done by a fermentation with yeast in methods of the present invention. The formation of ethanol from the sugars can be accomplished by yeasts such as *Saccharomyces cerevisiae*, such as described in U.S. Pat. Nos. 2,802,774, and *Fusarium oxysporum*. Other useful microorganisms are the ethanol-producing *bacillus* described, for example, U.S. Pat. No. 4,094,742, which are all incorporated herein in their entireties by reference. The concentration of enzyme (from e.g., *Saccharomyces cerevisiae*) added for fermenting sugars can be, for example, from about 0.001% to about 2% by weight enzyme, or from about 0.01% to about 1% by weight enzyme, or from about 0.015% to about 0.5% by weight enzyme, or from about 0.2% to about 0.75% by weight enzyme, or from about 0.1% by weight to about 0.5% by weight enzyme, or from about 0.2% to about 0.4% by weight enzyme, based on fermentable material on solids weight basis, though other amounts may be used.

The nonoxidizing biocide used for control of bacteria during (and/or before and/or after) fermentation in methods of the present invention can be, for example, dibromonitrilopropionamide (e.g., 2,2-dibromo-3-nitrilopropionamide), bromo-nitroalkane-diols (e.g., 2-bromo-2-nitropropane-1,3-diol), methylene bisthiocyanate, 2-(thiocyanomethyl-thio) benzothiazole, cyanodithiocarbimate salts, N-methyldithiocarbamate salts, poly[oxyethylene(dimethyliminio)-ethylene (dimethyliminio)ethylene dichloride, tetrakishydroxymethylphosphoniumsulfate, 1,1,1-tris(hydroxymethyl)nitromethane, glutaraldehyde, 1,5-pentanedial, alkylbenzyl ammonium chloride, 2-bromo-2-nitro-propane-1,3-diol, didecyl dimethyl ammonium chloride, dimethyldithiocarbamate salts, dodecylguanidine hydrochloride, 1,2-benzisothiazoline-3-one, 5-chloro-2-methyl-4-isothiazolin-3-one, 2-methyl-4-isothiazoline-3-one, n-octyl isothiazolinone, dichloro-n-octylisothiazolinone, bromonitrostyrene, tetrahydro-3,5-dimethyl-2H-1,3,5-thiadiazine-2-thione, or any combinations thereof. The nonoxidizing biocide can be, for example, dihalonitrilopropionamides (e.g., 2,2-dihalo-3-nitrilopropionamides), including, but not limited to, the dibromonitrilopropionamides (e.g., 2,2-dibromo-3-nitrilopropionamide), dichloronitrilopropionamides (e.g., 2,2-dichloro-3-nitrilopropionamide), diiodonitrilopropionamides (e.g., 2,2-diiodo-3-nitrilopropionamide), difluoronitrilopropionamides (e.g., 2,2-difluoro-3-nitrilopropionamide), or any combinations thereof. Other examples include but are not limited to, hydroxypropyl methanethiosulfonate (HPMTS) and/or 2,2-dibromo-3-nitrilopropionamide (DBNPA) with or without other biocides. For any of the compounds or compositions identified throughout, it is understood that the specific halide can be replaced with a different halide. For instance, bromo can be replace by chloro or iodo, and vice versa.

Treatment rates of nonoxidizing biocide on the fermentation mash should be a concentration sufficient to control the problematic bacteria to the fermentations without reducing the yeast. The concentration generally is not otherwise limited. The concentration of nonoxidizing biocide used to treat a fermentation mash can be, for example, at least about 0.1 ppm, or at least about 1 ppm, or at least about 10 ppm, or from about 0.1 ppm to about 1000 ppm, or from about 50 ppm to about 500 ppm, or from about 75 ppm to about 250 ppm, or from about 100 ppm to about 200 ppm, based on fermentable mash, on a dry solids weight/weight basis, though other concentrations may be used. For example, treatment of fermentable mash with 1 ppm biocide would be equivalent to treatment with 1 pound biocide per 1,000,000 pounds of fermentable mash. The concentration of nonoxidizing biocide which can be used to treat a fermented mash at the beer well can be similar to the indicated levels used on the fermentation mash at the fermentation vessel, or other concentrations. The concentration of nonoxidizing biocide used to treat process water recycled to the fermenter, such as recycled thin stillage, recycled scrubber effluent, and/or recycled condensed vapors from grain drying, can be the same or similar to the indicated levels used on the fermentation mash at the fermentation vessel, or other concentrations.

The stabilized oxidizer that can be used for bacteria control in the present fermentation methods can be an oxidizer material that has been synthesized, formulated, or otherwise modified such that it releases oxidizing byproducts of the material at a slower rate than originally. The stabilizer oxidizer may be, but not necessarily be, selective to bacteria.

The stabilized oxidizer used for control of bacteria can be stabilized hypochlorous acid, stabilized hypochlorite, stabilized choramine, stabilized hypobromous acid (e.g., stabilized as a brominated sodium sulfamate or as any other stabilized form), stabilized chlorine dioxide (e.g., a slowly released $ClO_2$), stabilized peracetic acid (e.g., a slowly released $H_3C$—OOOH), iodine or stabilized iodine products (e.g., a solid iodine or iodide or a electronlytically generated iodine), slow releasing chlorine trione, slow releasing sodium trichloro-s-triazinetrione, slow releasing sodium dichloro-s-triazinetrione (e.g., a slow releasing oxidizer than can kill bacteria but would be stopped before it kills yeast), slow releasing chlorine trione, slow releasing sodium triochloro-s-triazinetrione, a stabilized chlorohydantoin, a stabilized bromohydantoin, or a stabilized modified hydantoin, or any combinations thereof.

These stabilized oxidizers can be formulated as preparations of the type that retard the rate of release of oxidizing byproducts of the material, such as, for example, microgranules or buffered compounds. Stabilized chlorine dioxide can be, for example, a buffered sodium chlorite. The acidic nature of bacteria in the fermenter, e.g., lactic acid, may convert sodium chlorite to chlorine dioxide, which is an antibacterial agent that can degrade to nontoxic components of chloride and sodium ions (salts) with no free chlorine or dioxins produced in the process. In liquids, the stabilizers may be sulfamic acid-based or ammonium salt based. As indicated, some oxidizers can be stabilized in a solid form.

Treatment rates of stabilized oxidizer on the mash should be a concentration sufficient to control the problematic bacteria to the fermentations without reducing the yeast. The concentration generally is not otherwise limited. The concentration of stabilized oxidizer used to treat a fermentation mash can be, for example, at least about 0.1 ppm, or at least about 1 ppm, or at least about 10 ppm, or from about 0.1 ppm to about 1000 ppm, or from about 50 ppm to about 500 ppm, or from about 75 ppm to about 250 ppm, or from about 100 ppm to about 200 ppm, based on fermentable material, on a dry solids weight/weight basis, though other concentrations may be used. The concentration of stabilized oxidizer used to treat a fermented mash at the beer well can be the same or similar to the indicated levels used on the fermentation mash at the fermentation vessel, or other concentrations. The concentration of stabilized oxidizer used to treat process water recycled to the fermenter, such as recycled thin stillage, recycled scrubber effluent, and/or recycled condensed vapors from grain drying, can be the same or similar to the indicated levels used on the fermentation mash at the fermentation vessel, or other concentrations.

As an option, any process or composition of the present invention can include one or more antibacterial peptides, e.g., polycyclic antibacterial peptides, such as Nisin. The peptide(s) can be present in any amount, such as from about 0.01 ppm to 500 ppm or more, wherein this amount is the concentration present during start of fermentation (e.g., in the fermenter) or can be based on the weight of overall composition that is added to the process. As an option, the one or more polycyclic antibacterial peptides can be present in a weight ratio of (polycyclic antibacterial peptide) to (nonoxidizing biocide and/or stabilized oxidizer) of from 1:2 to 1:1,000, such as 1:5 to 1:500, or 1:10 to 1:250, or 1:20 to 1:200, or 1:30 to 1:100, or 1:40 to 1:100, or 1:50 to 1:150, or other ratios within these ranges or outside of these ranges.

As an option, one or more polycyclic antibacterial peptides when combined with one or more biocides as described herein, can provide synergistic results in preventing or controlling bacteria, especially *Lactobacillus* sp. In other words, the combination can be effective, especially in a synergistic way, in preventing or controlling microbial spoilage or contamination in ethanol fermentation systems or processes, such as exemplified herein.

Figure 3:
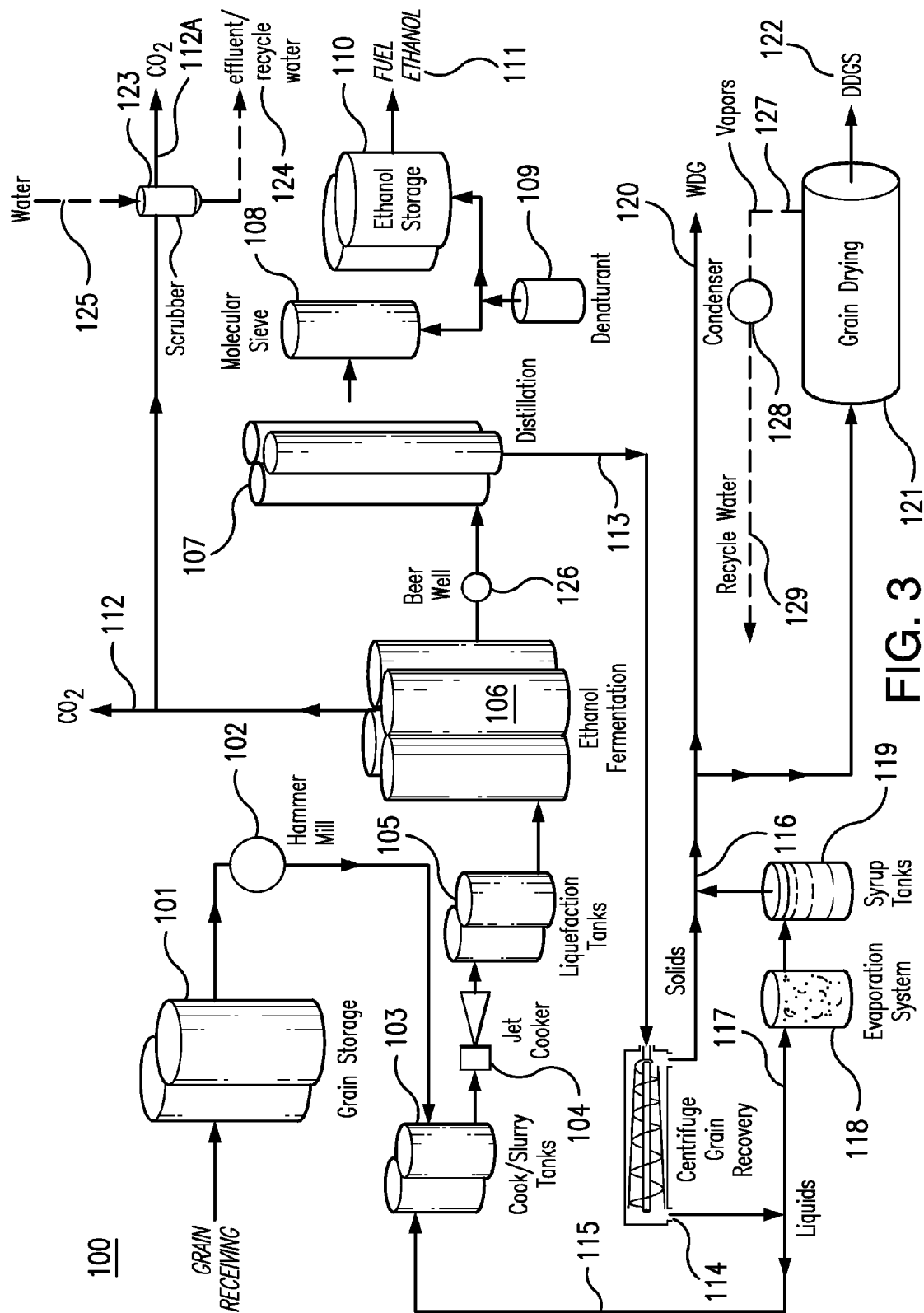
FIG. 3 illustrates another process flow diagram of a method of ethanol production in a production plant with introduction of a non-antibiotic biocide for control of bacteria according to an embodiment of the present invention.

A method according to the present invention can be practiced in conventional ethanol production plants with modifications that can be easily made in view of the present invention. Referring to FIG. 3, an ethanol production plant (100) based on a dry mill process is shown on which the method of the present invention can be utilized with adaptations. Grain can be delivered to an ethanol plant where it can be loaded in storage bins (101) designed to hold enough grain to supply the plant for at least one production run. The grain can be screened to remove debris and ground into coarse flour, such as by milling (102). The flour can be cooked and liquefied. During the cook process (103), the starch in the flour is physically and chemically prepared for fermentation. The milled grain can be mixed with process water, the pH can be adjusted to acidic pH, such as about 5.5 to about 6.0, and an alpha-amylase enzyme can be added. The slurry can be heated to about 180-190° F. for about 30-45 minutes to reduce viscosity. The resulting slurry can be then pumped through a pressurized jet cooker (104) at about 221° F. and held for about 5 minutes. The mixture can be then cooled by an atmospheric or vacuum flash condenser. After the flash condensation cooling, the mixture can be held in a liquefaction tank for about 1-2 hours at about 180-190° F. to give the alpha-amylase enzyme time to break down the starch into short chain dextrins. After pH and temperature adjustment, a second enzyme, glucoamylase, can be added as the mixture is pumped into the fermentation tanks. Once inside the fermentation tanks, the mixture is referred to as mash. The glucoamylase enzyme breaks down the dextrins to form simple sugars suitable for fermentation reaction. For fermentation (106), yeast is added to convert the sugar to ethanol and carbon dioxide. The nonoxidizing biocide is combined with the mash in the first fermentation tank. The amount of nonoxidizing biocide or stabilized oxidizer can vary depending on the particular agent. The amount added can be effective to eradicate or control an existing bacteria infection of the plant or prevent an outbreak of bacteria without reducing yeast. The mash can be allowed to ferment for about 24-60 hours at from about 70° F. to about 115° F., or from about 80° F. to about 100° F., resulting in a mixture that contain up to about 15% ethanol as well as the solids from the grain and added yeast. Also, as starting yeast fermentations at a pH of 5.6 to 6.0 may result in a higher risk of microbial contamination, the pH after liquefaction can be adjusted down to a pH less than 5.0 using for example dilute acid (e.g. sulfuric acid). The fermented mash can be pumped into a distillation unit, such as a multi-column distillation system, where additional heat is added for distillation (107). One or more beer wells (126) can be used as a reservoir to store fermented mash as a feed supply to the distillation columns. The distillation columns can use the differences in the boiling points of ethanol and water to boil off and separate the ethanol. By the time the product stream is ready to leave the distillation columns, it can contain about 95% ethanol by volume (190-proof). The residue from this process, called stillage, contains non-fermentable solids and water and can be pumped out from the bottom of the columns into the centrifuges or other filtering means. The 190-proof ethanol still can contain about 5% water. It can be passed through a molecular sieve (108) to physically separate the remaining water from the ethanol based on the different sizes of the molecules, or otherwise processed in other conventional manners used to separate the water content from the ethanol. This step can produce 200-proof anhydrous (waterless) ethanol. Before the ethanol is sent to storage tanks (110), a small amount of denaturant (109) can be added, making it unfit for human consumption. The fuel ethanol (111) contains no biocide or antibiotic. During the ethanol production process, two commercially valuable coproducts are created: carbon dioxide and distillers grains. As yeast ferment the sugar, they release large amounts of carbon dioxide gas (112), with other fermentation gases such as volatile organic compounds and water vapor. As indicated, the carbon dioxide can be released to the atmosphere as directly vented carbon dioxide (112) (as one option), or the carbon dioxide (112A) can be purified with a scrubber (123) before release or capture (as another option). The scrubber (123) can be used to remove volatile organic compounds (including, e.g., ethanol) from the fermentation gas. Scrubbers contact the fermentation gases (typically mostly carbon dioxide) with water (125) to remove pollutants and to recover ethanol that would otherwise be lost due to evaporation from the fermenter. The aqueous effluent from the scrubber (123) can be recycled as a source of process water for fermentation. As indicated, if recycled as a water source for fermentation, the scrubber effluent (124) optionally can be treated with the nonoxidizing biocide and/or stabilized oxidizer before re-introduction into the process system. The purified carbon dioxide from the scrubber optionally can be captured and marketed to the food processing industry for use in carbonated beverages and flash-freezing applications. The stillage (113) (e.g., whole stillage) from the bottom of the distillation tanks contains solids from the grain and added yeast as well as liquid from the water added during the process. It can be sent to centrifuges (114) for separation into thin stillage (115) (a liquid with about 5-10% solids) and a solids containing fraction (116) that can be processed into distillers grains. Some of the thin stillage (115) can be routed back to the cook/slurry tanks as makeup water, reducing the amount of fresh water required by the cook process. As indicated, if recycled as a water source for fermentation, the thin stillage (115) optionally can be treated with the nonoxidizing biocide and/or stabilized oxidizer before re-introduction into the process system. The addition of thin stillage to the slurry often necessitates the need for pH adjustment of the slurry. For example, when milled whole ground corn grain is used as a starch-containing material and mixed with water, the pH of the slurry can be, for example, about pH 5.8 to about pH 6.2. However, the pH of the slurry can be reduced by the addition of thin stillage to about pH 4.8 to pH 5.2, which can destabilize saccharification agents. Therefore, when reusing liquid stillage, the pH of the slurry can be adjusted to about pH 5.6 to 6.0 using suitable alkali (e.g., sodium or calcium hydroxide, sodium carbonate or ammonia). The rest (117) of the stillage can be sent through a multiple-effect evaporation system (118) where it can be concentrated into syrup (e.g., 25-50% solids) (119). This syrup, which is high in protein and fat content, can be then mixed back in with solids containing fraction (116) to provide wet distillers grain (WDG) (120). With the added syrup, the WDG still contains most of the nutritive value of the original feedstock plus the added yeast, so it makes an excellent livestock ration for local feedlots and dairies, or other types of animal feeds. After the addition of the syrup, it can be conveyed to a wet cake pad as WDG (120), where it can be loaded for transport. Many ethanol facilities do not have enough nearby livestock to utilize all of the WDG. To avoid spoilage, the WDG usually is used soon after it is produced. Therefore, it is commonly sent through a drying system (121) to remove moisture and extend its shelf life. Conventional drying practices that can be used in this respect comprise indirect steam at a pressure of 100 to 250 psia or hot flue gas to provide heat for drying. The vapors (127) produced in the dryer can be condensed, such using a condenser (128) (e.g., a heat exchanger) to form an aqueous byproduct, or, alternatively, can be vented into the atmosphere (not shown). As indicated, the condensed vapors (129) can be used as recycled process water for the fermentation system, such as a water source for the fermentation vessel(s). As also indicated, if recycled as a water source for fermentation, the condensed vapors (129) optionally can be treated with the nonoxidizing biocide and/or stabilized oxidizer before re-introduction into the process system. This resulting distillers dried grains with solubles (DDGS) (122) is commonly used as a high-protein ingredient in animal feed, such as feed for cattle, swine, poultry, and fish. Although useful as a continuous or semi-continuous process with respect to FIG. 3, the ethanol fermentation process of the present invention also can be conducted batch-wise.

As another illustration, dibromonitrilopropionamide (e.g., 2,2-dibromo-3-nitrilopropionamide) or other dihalonitrilopropionamide can be the antibiotic alternative used for bacteria control in an ethanol fermentation process, such as those shown in FIGS. 1, 2 and 3, although not limited thereto. Commercial sources of 2,2-dibromo-3-nitrilopropionamide (DBNPA) include, for example, BRONAM® 20, which is commercially available from Buckman Laboratories International, Inc., Memphis Term. During the fermentation process, the DBNPA can be diluted into tanks (stirred) where fermentation takes place for about 24-48 hours at about 90-95° F. Treatment rates of DBNPA of from about 50 ppm to about 500 ppm, or from about 100 ppm to about 200 ppm (as product based on the active ingredient), or other ranges, can control lactobacilli, but not affect yeast(s) in the fermentation process so that the antimicrobial does not end up in the DDGS. The fermentation process can involve, for example, from about 600,000 to about 1 million gallons of process material per production run. Then the ferment is pumped to the "beer well" for about 2-3 hours, which can be as long as about 20 hours in beer at about 105° F., and, thereafter, it is distilled. DBNPA preferably is added to the first fermentation tank (if multiple tanks are used) and this active ingredient is allowed to react, and then break down over about 24-48 hours. The DBNPA can be introduced to the first fermentation tank directly, or via recycled process water as indicated, or other introduction methods. Fermented mash in the beer well and/or portions of the beer well that come into contact with the fermented mash (e.g., inner tank walls), can be treated with DBNPA. The concentration of DBNPA used to treat a fermented mash at the beer well can be similar to the indicated levels used at the fermentation tank.

Under the conditions in the fermentation tank, DBNPA is expected to last intact only about 1-2 hours, based on laboratory work. The stillage, i.e., fermented unevaporated product (post "beer tank") of distillation, is centrifuged, and dried (e.g., about 1 hour at about 250-300° F.), then the mixture is pumped over to a final tank where it is called the DDGS. DDGS is about ⅓ mass of the starting raw material for corn. The chemistry of DBNPA is not expected to endure and survive the centrifugation and heat of drying prior to entering distillers dried grains with solubles (DDGS) stage. In the corn-to-ethanol process, for example, DBNPA is expected to degrade to carbon dioxide and water vapor, and, as such, would have low environmental impact. Based on experimental results, DBNPA kills the bacteria (lactobacilli), but does not kill the yeast involved in fermentation, nor is DBNPA believed to carry over into the DDGS. The application of DBNPA avoids the use of antibiotics, which can remain stable throughout the process. The use of DBNPA makes the use of antibiotics unnecessary. The use of DBNPA is more economical since the cost of antibiotics (as the only treatment widely employed) can be relatively high and costly to the fermentation. Moreover, DBNPA makes possible an increase in ethanol yield, e.g., from about 0.5% to about 5 by weight, or from about 1% to about 4% by weight, or from about 1% to about 3.5% by weight, or from about 1.25% to about 2.5% by weight, or from about 2% to about 3% by weight, or other increases, as compared to untreated infected fermented mashes, which is obviously a benefit to the processor.

The present invention can provide, for example, for antibiotic-free conversion of biomass to fuel grade alcohol, which can be blended with no-lead gasoline to produce "gasohol" fuel or other combustions fuels. The methods of the present invention are also applicable to production of food grade ethanol. The unexpected activity of non-antibiotic biocides as shown herein in fermentation processes has been confirmed using standard laboratory techniques as illustrated herein.

The present invention includes the following aspects/embodiments/features in any order and/or in any combination:

1. The present invention relates to a method for producing ethanol by fermentation comprising:
   a) fermenting a fermentable mash in the presence of at least one nonoxidizing biocide, and yeast in a vessel to produce ethanol and a solids content, wherein said nonoxidizing biocide controls growth of bacteria in the mash without reducing yeast population; and
   b) distilling the fermented mash to separate at least a portion of the ethanol from said solids content.

2. The method of any preceding or following embodiment/feature/aspect, further comprising obtaining a distillers dried grains product from said solid contents containing less than about 100 ppm of the nonoxidizing biocide.

3. The method of any preceding or following embodiment/feature/aspect, wherein the fermented mash in step (b) contains no greater than 10 ppm antibiotic.

4. The method of any preceding or following embodiment/feature/aspect, wherein said fermented mash in step b) has less than about 10 ppm of nonoxidizing biocide present after distillation.

5. The method of any preceding or following embodiment/feature/aspect, wherein said fermented mash in step b) has less than about 1 ppm of nonoxidizing biocide present after distillation.

6. The method of any preceding or following embodiment/feature/aspect, wherein the bacteria are *Lactobacillus* sp., *Acetobacter* sp., or combinations thereof.

7. The method of any preceding or following embodiment/feature/aspect, wherein the bacteria are obligate anaerobes.

8. The method of any preceding or following embodiment/feature/aspect, wherein the fermented mash in step (a) has at least about 5-fold less lactic acid on a weight % basis than the same fermented mash fermented in the absence of the nonoxidizing biocide.

9. The method of any preceding or following embodiment/feature/aspect, wherein the fermented mass in step (a) has at least about 5-fold less acetic acid on a weight % basis than the same fermented mash fermented in the absence of the nonoxidizing biocide.

10. The method of any preceding or following embodiment/feature/aspect, wherein the nonoxidizing biocide is 2,2-dibromo-3-nitrilopropionamide, methylene bisthiocyanate, 2-(thiocyanomethyl-thio)benzothiazole, cyanodithiocarbimate salt, N-methyldithiocarbamate salt, poly[oxyethylene(dimethyliminio)-ethylene (dimethyliminio)ethylene dichloride, tetrakishydroxymethylphosphoniumsulfate, 1,1,1-tris(hydroxymethyl)nitromethane, glutaraldehyde, 1,5-pentanedial, alkylbenzyl ammonium chloride, 2-bromo-2-nitro-propane-1,3-diol, didecyl dimethyl ammonium chloride, dimethyldithiocarbamate salt, dodecylguanidine hydrochloride, 1,2-benzisothiazoline-3-one, 5-chloro-2-methyl-4-isothiazolin-3-one, 2-methyl-4-isothiazoline-3-one, n-octyl isothiazolinone, dichloro-n-octylisothiazolinone, bromonitrostyrene, or tetrahydro-3,5-dimethyl-2H-1,3,5-thiadiazine-2-thione, or any combinations thereof 11. The method of any preceding or following embodiment/feature/aspect, wherein the nonoxidizing biocide is a dihalonitrilopropionamide.

12. The method of any preceding or following embodiment/feature/aspect, wherein the nonoxidizing biocide is 2,2-dibromo-3-nitrilopropionamide.

13. A method for producing ethanol with fermentation comprising:
   a) fermenting a fermentable mash in the presence of at least one stabilized oxidizer, and yeast in a vessel to produce ethanol and a solids content, wherein said stabilized oxidizer controls growth of bacteria in the mash without reducing yeast population; and
   b) distilling the fermented mash to separate at least a portion of the ethanol from the solids content of the fermented mash.
14. The method of any preceding or following embodiment/feature/aspect, further comprising obtaining a distillers dried grains product from said solid contents containing less than about 100 ppm of the stabilized oxidizer.
15. The method of any preceding or following embodiment/feature/aspect, wherein the stabilized oxidizer is stabilized hypochlorous acid, stabilized hypochlorite, stabilized choramine, stabilized hypobromous acid (e.g. bromosulfamate), stabilized chlorine dioxide, stabilized peracetic acid, iodine, stabilized iodine products, slow releasing chlorine trione sodium triochloro-s-triazinetrione, slow releasing sodium dichloro-s-triazinetrione, slow releasing chlorine trione, slow releasing sodium trichloro-s-triazinetrione, stabilized chlorohydantoin, stabilized bromohydantoin, or a stabilized modified hydantoin, or any combinations thereof.
16. The method of any preceding or following embodiment/feature/aspect, wherein the fermented mash in step (b) contains no greater than 10 ppm antibiotic.
17. The method of any preceding or following embodiment/feature/aspect, wherein said fermented mash in step b) has less than about 10 ppm of stabilized oxidizer present after distillation.
18. The method of any preceding or following embodiment/feature/aspect, wherein said fermented mash in step b) has less than about 1 ppm of stabilized oxidizer present after distillation.
19. The method of any preceding or following embodiment/feature/aspect, wherein the bacteria is a *Lactobacillus* sp., *Acetobacter* sp., or any combinations thereof.
20. The method of any preceding or following embodiment/feature/aspect, wherein the bacteria are obligate anaerobes.
21. The method of any preceding or following embodiment/feature/aspect, wherein the fermented mash in step (a) has at least about 5-fold less acid on a weight % basis than the same fermented mash fermented in the absence of the stabilized oxidizer biocide, wherein the acid is lactic acid or acetic acid.
22. A method for producing ethanol with fermentation comprising:
   a) providing fermentable mash, at least one non-antibiotic biocide, and at least one yeast as a mixture in a vessel under conditions wherein fermentation of the mash occurs to produce ethanol and the at least one non-antibiotic biocide controls growth of bacteria in the mash without killing the yeast, wherein the non-antibiotic biocide is a nonoxidizing biocide, stabilized oxidizer, or combination thereof;
   b) distilling the fermented mash to separate at least a portion of the ethanol from a solids content of the fermented mash.
23. A method for producing ethanol with fermentation comprising:
   a) fermenting a fermentable mash in the presence of at least one yeast in a vessel to produce ethanol and a solids content;
   b) storing at least a portion of the fermented mash in at least one beer well in the presence of at least one nonoxidizing biocide, wherein the nonoxidizing biocide controls the growth of bacteria in the at least one beer well; and
   c) feeding stored mash from the at least one beer well to at least one distillation unit;
   d) distilling the fermented mash in the at least one distillation unit to separate at least a portion of the ethanol from the solids content.
24. A method for producing ethanol comprising:
   a) fermenting a fermentable mash in the presence of yeast and recycled process water in a fermenter vessel to produce fermented mash comprising ethanol and a solids content;
   b) optionally scrubbing gaseous emissions from the fermenter vessel with an aqueous solution and recycling at least a portion of the scrubber effluent solution into the fermenter vessel;
   c) optionally storing at least a portion of the fermented mash in at least one beer well;
   d) feeding fermented mash to a distillation unit;
   e) distilling the fermented mash in the distillation unit to separate at least a portion of the ethanol from stillage;
   f) separating the stillage into a liquids-containing fraction and a solids-containing fraction;
   g) optionally recycling at least portion of the liquids-containing fraction of f) into the fermenter vessel,
   h) recovering the solids-containing fraction of f) as at least in part as wet distillers grains product and/or drying at least a portion of the solids-containing fraction to produce distillers dried grains product and evaporated vapors;
   i) optionally condensing the evaporated vapors of h) and recycling at least a portion of the condensed vapors into the fermenter vessel, and
   wherein nonoxidizing biocide and/or stabilized oxidizer is added to or is present in at least one source of recycled water of the scrubber effluent solution of b), the liquids-containing fraction from stillage separation of f), and condensed vapors from distillers grains drying of i), or any combinations thereof, before the water source is recycled into the fermenter vessel.
25. A method for producing distillers dried grains coproducts of ethanol production comprising:
   a) fermenting a fermentable mash in the presence of yeast in a fermenter vessel to produce fermented mash comprising ethanol and a solids content;
   b) optionally scrubbing gaseous emissions from the fermenter vessel with an aqueous solution and recycling at least a portion of the scrubber effluent solution into the fermenter vessel;
   c) optionally storing at least a portion of the fermented mash in at least one beer well;
   d) feeding fermented mash to a distillation unit;
   e) distilling the fermented mash in the distillation unit to separate at least a portion of the ethanol from stillage;
   f) separating the stillage into a liquids-containing fraction and a solids-containing fraction;
   g) optionally recycling at least portion of the liquids-containing fraction of f) into the fermenter vessel,
   h) recovering the solids-containing fraction of f) with drying of at least a portion of the solids-containing fraction to produce distillers dried grains product and evaporated vapors;
   i) optionally condensing the evaporated vapors of h) and recycling at least a portion of the condensed vapors into the fermenter vessel, and
   wherein nonoxidizing biocide and/or stabilized oxidizer for control of bacteria in the fermentation vessel is added to or is present in at least one of the fermenter vessel, beer well, and recycled sources of water, or any combinations thereof 26. The method of any preceding or following embodiment/feature/aspect, further comprising obtaining a distillers dried grains product containing less than about 100 ppm of the nonoxidizing biocide and/or stabilized oxidizer.
27. The method of any preceding or following embodiment/feature/aspect, wherein said fermenting occurs also in the presence of at least one antibacterial peptide.
28. The method of any preceding or following embodiment/feature/aspect, wherein said fermenting occurs also in the presence of at least one polycyclic antibacterial peptide.
29. The method of any preceding or following embodiment/feature/aspect, wherein said non-oxidizing biocide and said polycyclic antibacterial peptide are synergistic with regarding to biocidal control of at least one bacteria during and/or after fermentation to produce ethanol.
30. A composition comprising at least one non-oxidizing biocide and at least one polycyclic antibacterial peptide.
31. The composition of any preceding or following embodiment/feature/aspect, wherein said non-oxidizing biocide and said polycyclic antibacterial peptide are present in a synergistic amount to with regard to controlling at least one bacteria during a fermentation to produce ethanol.
32. The composition of any preceding or following embodiment/feature/aspect, wherein said non-oxidizing biocide is 2-bromo-2-nitropropane-1,3 diol or 2,2-dibromo-3-nitrilopropionamide or a halide analog thereof.

The present invention can include any combination of these various features or embodiments above and/or below as set forth in sentences and/or paragraphs. Any combination of disclosed features herein is considered part of the present invention and no limitation is intended with respect to combinable features.

The following examples are intended to illustrate, not limit, the present invention. In the following examples, all parts are proportions by weight unless otherwise specified.

EXAMPLES

Example 1

Experiments were conducted to evaluate the effectiveness of a nonoxidizing biocide as an antimicrobial agent for control of *Lactobacillus* infections in ethanol fermentation. The nonoxidizing biocide was BRONAM® 20 (20% 2,2-dibromo-3-nitrilopropionamide). The lactobacilli was *L. plantarum*. The yeast was *Saccharomyces cereviseae*. Corn mashes containing approximately 30% (w/w) dry solids were used.

Experimental Procedures

For slurry preparation, the moisture of ground corn was determined gravimetrically using a moisture balance by measuring the mass loss that occurred upon drying. The amount of corn, deionized (DI) water, and enzyme needed to prepare 160 g of corn slurry at a total dry solids concentration of 30% (w/w) for each replicate was determined. For each treatment, three independent replicate slurries were prepared by weighing the required amount of DI water into labeled Labomat beakers, followed by addition of the required mass of corn flour. The alpha-amylase enzyme (Liquozyme SC DS, Novozymes) was diluted to ensure more precise delivery of enzyme to each flask. A 0.13-g/ml working solution of the alpha amylase was used and added at a dose of 0.02% (w/w) based on the wet weight of the corn. The slurries were hand swirled after all components were in the Labomat beakers. Sealed beakers were attached to a vertically mounted wheel in the Labomat (Model BFL12 805, Mathis, Switzerland), which rotated at 50 rpm during the incubation. The wheel was programmed to reverse direction every 50 seconds to improve the mixing efficiency. Samples were liquefied by incubating at 83° C. for 90 minutes, after which the samples were cooled to 40° C. in the Labomat.

For fermentation, once the mash was cooled, the entire contents (approximately 160 g) of each Labomat beaker were transferred to a sterile 250-ml Erlenmeyer flask. The masses of the mash and flasks were recorded, and the mass of mash transferred to the fermentation flasks was calculated. The pH of the mash was adjusted to <5.2 by addition of 150 μl of 10 N sulfuric acid. The flasks were shaken at 170 rpm on an incubator/shaker (Sartorius, Certomat BS-1) at 32° C. until preparation of all mashes was complete.

All enzymes, nutrients, and other amendments added to the fermentation flasks were freshly prepared before use. The yeast nutrients (AYF1177; Ethanol Technology, Milwaukee, Wis.) were prepared as a 0.2-g/ml solution, and a dose of 1500 ppm (w/w, based on the wet weight of corn) was used. Urea was added as a sterile 0.2-g/ml solution to a final concentration of 500 ppm as nitrogen (w/w, based on the total mass of mash). The glucoamylase enzyme (Spirizyme Fuel, Novozymes) was prepared as a 0.25-g/ml solution and added at a dose of 0.015% (w/w, based on the wet weight of corn).

The *L. plantarum* culture was prepared for inoculation by growing throughout the day in 100-ml of MRS broth. The amount of culture needed to achieve an initial concentration of $10^7$ CFU/ml in the corn mash was estimated from growth-curve data for *L. plantarum* in MRS broth. The initial concentration of the bacteria was determined by plating serial dilutions of the culture on MRS agar containing cycloheximide and incubating at 32° C. for 2 days before counting colonies. The fermentation flasks were inoculated with 0.5 ml of this *L. plantarum* culture, which had a bacterial cell concentration of $2 \times 10^9$ CFU/ml. This gave an initial concentration of $6 \times 10^6$ CFU/ml, which is slightly lower than the target concentration but sufficient for the purposes of this study.

After inoculating with bacteria, the fermentation flasks were fitted with sanitized fermentation traps and incubated at 32° C. with shaking at 170 rpm for 1 hour. This simulates the typical time between the beginning of a fermentor fill and inoculation with yeast in full-scale fuel-ethanol facilities.

A 0.2-g/ml suspension of yeast (*Saccharomyces cerevisiae*; Ethanol Red; Fermentis, Marcq-en-Baroeul, France) was prepared in a sterile 250-ml flask. This suspension was incubated and mixed for 20 minutes at 40° C. before inoculation into the fermentation flasks. Each fermentation flask was inoculated with 160 μl of the yeast suspension to attain an initial concentration of $10^7$ yeast cells/ml. After the initial 1-hr incubation with bacteria, the flasks were inoculated with yeast and dosed with BRONAM® 20. The treatments (bacteria and BRONAM® 20 dose) used in this study to investigate the effectiveness of BRONAM® 20 in controlling infections by lactic acid bacteria in fuel-ethanol fermentations are shown in Table 1.

TABLE 1

| Treatment ID | inoculation | BRONAM ® 20 concentration* (ppm) | corn dry solids concentration (%, w/w) |
|---|---|---|---|
| infection-free control (IFC) | yeast | 0 | 30 |
| infected control (IC) | yeast + *L. plantarum* | 0 | 30 |
| BRONAM ® 20-50 | yeast + *L. plantarum* | 50 | 30 |

TABLE 1-continued

| Treatment ID | inoculation | BRONAM® 20 concentration* (ppm) | corn dry solids concentration (%, w/w) |
|---|---|---|---|
| BRONAM® 20-100 | yeast + L. plantarum. | 100 | 30 |
| BRONAM® 20-200 | yeast + L. plantarum | 200 | 30 |

The mass of each flask was recorded after all additions were made, and the sanitized fermentation traps were reinserted into each flask. The mass of each flask with the trap in place was also recorded. The flasks were incubated at 32° C. with shaking at 170 rpm in an incubator/shaker (Sartorius, Certomat BS-1) for 61 hours. The mass of each flask with the traps in place were measured periodically throughout fermentation to estimate the rate of fermentation (the mass of the fermentation flasks decreases when carbon dioxide is lost by bubbling out of the fermentation traps).

After incubation for 61 hours, the mass of each flask was measured before and after removing the trap. While hand swirling, 1.0 ml of mash was pipetted from each sample and transferred to a test tube containing 9.0 ml of 0.05 M phosphate buffer. These samples were then serially diluted to achieve dilution factors of $10^5$ to $10^7$. One-hundred microliters of each of the highest three dilutions was then plated on MRS agar to estimate the final concentration of L. plantarum in each flask. The plates were incubated for 2 days at 32° C. before attempting to count colonies.

Each flask was mixed with an overhead agitator and samples were collected for the following measurements: yeast cell counts, final concentrations of substrates (glucose, DP2, DP3, and DP4+, where "DPx" represent glucose oligomers with "x" subunits), fermentation products (ethanol, glycerol, lactic acid, and acetic acid), total dry solids, and dissolved dry solids, and the density of the beer liquid phase. All measurements were made using standard operating procedures. Samples were prepared for yeast cell counts by diluting at a factor of 100 in deionized water and staining with methylene blue to estimate viability then counted microscopically using a hemacytometer. The final concentrations of substrates and fermentation products were determined by HPLC. Samples were prepared for HPLC by centrifugation to remove large solids (8,000xg for 3 minutes) followed by filtration through 0.45-1 µm syringe filters, and acidification with sulfuric acid to a final concentration of 0.01 N. The total and dissolved solids concentrations were measured gravimetrically based on the mass loss during drying for 3 hours at 105° C. Samples were prepared for measurement of dissolved solids and liquid-phase density by centrifugation followed by filtration of the supernatant through 0.45-µm syringe filters. The density of the beer liquid phase was measured using an Anton-Parr densitometer.

Figure 4:
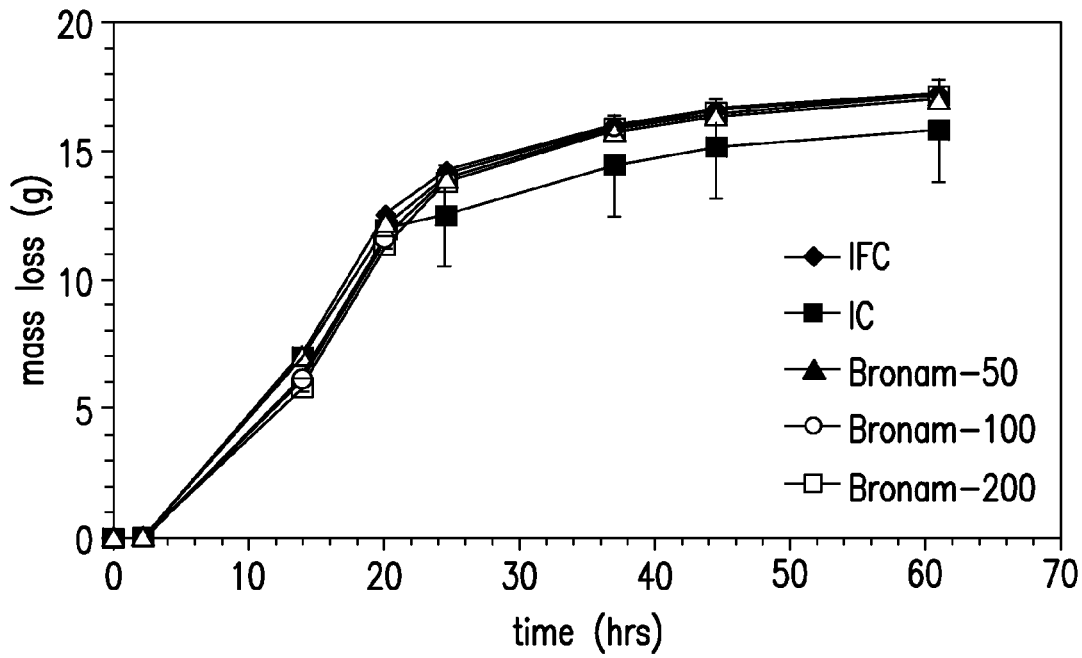
FIG. 4 shows fermentation progress based on mass loss (g) due to carbon dioxide production in fermentations over time (hours), where the fermentations are subjected to the nonoxidizing biocide treatments and nontreated controls in corn fermentation experiments as described in Example 1.

The fermentation rates for all treatments are shown in FIG. 4. One of the apparent differences among the treatments was the infected control (IC), which appeared to have a smaller total mass loss than the other treatments. This was entirely due to one fermentation flask, however, and its influence is shown by the large error bars for the IC treatment relative to the other treatments. Therefore, the difference in final mass loss is not considered to be statistically significant. It is also observed that the mass loss after about 16 hours seems to be slightly lower for the two highest BRONAM® 20 doses. Although these differences were reproducible and are statistically significant, it does not appear to be important, because the mass loss for these two treatments was identical to the infection free control (IFC) after 24 hours, which is only about half the industry standard incubation time.

Figure 5:
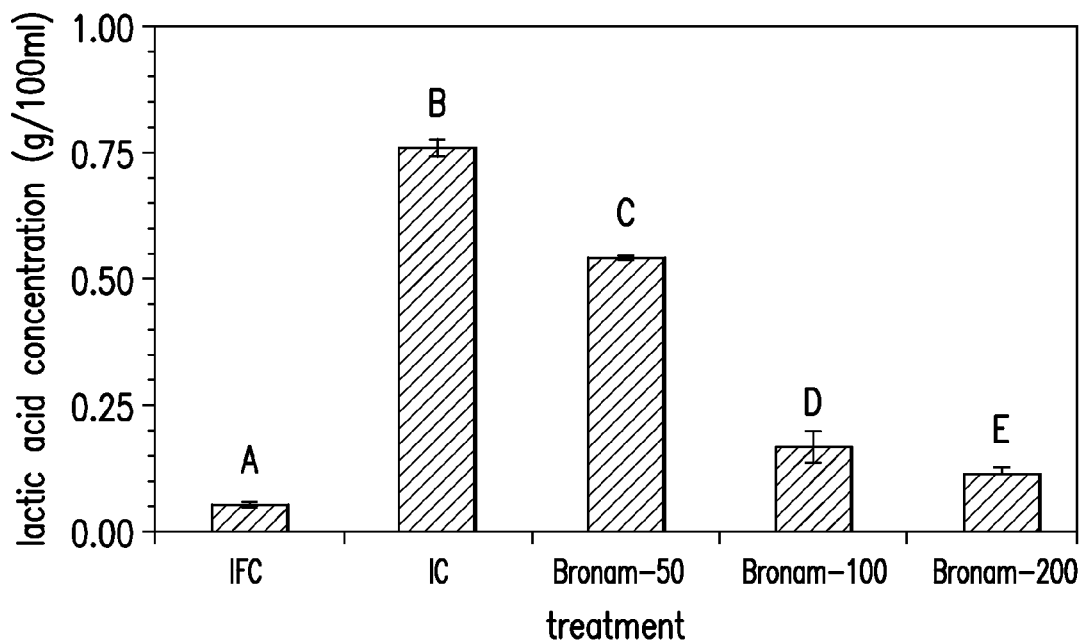
FIG. 5 shows final concentrations (g/100 mL) of lactic acid in fermentations subjected to the nonoxidizing biocide treatments and nontreated controls in corn fermentation experiments as described in Example 1.
Figure 6:
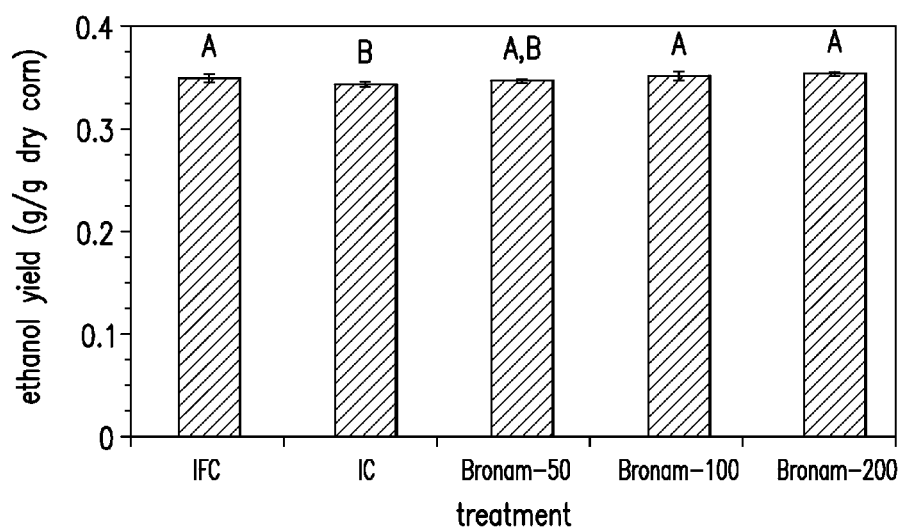
FIG. 6 shows ethanol yields (g ethanol/g dry corn) for the nonoxidizing biocide treatments and nontreated controls in corn fermentation experiments as described in Example 1, wherein bars that are labelled with the same letter are not significantly different from each other at the 95% confidence level.

The final concentrations of lactic acid and the ethanol yields for each treatment are shown in FIGS. 5 and 6. Analysis of variance (ANOVA) showed that significant differences existed among the treatments for both endpoints. Tukey's test for paired comparisons, which compares all possible pairs of treatments, was used to identify the significant differences, and these are shown by the labels on each bar in both figures. Any treatments that are labeled with the same letter are not significantly different from each other.

Obvious differences were observed in the final lactic acid concentrations, as shown in FIG. 5. The lowest concentration of lactic acid was observed in the IFC and the highest occurred in the IC. For example, infection of corn mashes with L. plantarum without the nonoxidizing biocide as in the infected control (IC) increased the final concentration of lactic acid nearly 14-fold in contrast to the infection free control (IFC). BRONAM® 20 reduced the amount of lactic acid that was produced at all doses, and there was a clear dose-response relationship. The lowest lactic acid concentration was observed for the infected corn mash treated with the 200-ppmv dose of BRONAM® 20, and this concentration was only slightly higher than was observed in the infection free control (IFC) ($0.11\pm0.01$ g/100 ml vs. $0.06\pm0.003$ g/100 ml for the IFC). The difference between the final lactic acid concentrations in the "Bronam-200" and IFC treatments was statistically significant: P=0.012, where P is the probability that the two concentrations are the same.). The inability of BRONAM® 20 to completely eliminate the increase in the final lactic acid concentration even at the highest dose may be due to the 1-hour incubation period between inoculation with lactic acid bacteria and addition of the antimicrobial compound.

The differences in ethanol yield observed were considered statistically significant and followed a pattern that is consistent with the trends shown in FIG. 5. The ethanol yield of the IC was significantly lower than the ethanol yield of all other treatments except for the "Bronam-50" treatment. Infection with L. plantarum in the infected control (IC) reduced the ethanol yield by about 2% relative to the infection-free control (IFC). Addition of BRONAM® 20 reduced the effects of bacterial infection at all tested dose levels relative to the infected control (IC), and at a concentration of at least 100 ppmv, the effects of bacterial infection were completely eliminated relative to the infected control (IC). With "Bronam-20," for example, an increase in ethanol yield was found to be 2.6% relative to the infected control (IC).

The results of this study clearly show that BRONAM® 20 is capable of controlling infections of Lactobacillus plantarum under fermentation conditions that are typical of those used in the fuel-ethanol industry. When mashes containing 30% (w/w) corn dry solids was infected with L. plantarum, the lactic acid concentration increased by more than 10-fold (from 0.06% to 0.76%, w/v) and the ethanol yield decreased by 2%. Treatment with BRONAM® 20 at a concentration of at least 100 ppm completely eliminated the effect of bacterial infection on ethanol yield and reduced the final lactic acid concentration by 80% or more relative to the infected control (IC).

Based on the results of this study, it was shown that nonoxidizing biocides, such as BRONAM® 20, can control bacterial infections in corn fermentation processes without killing yeast invaluable to the fermentation in fuel-ethanol production. Further in view of these results, that nonoxidizing biocides, such as BRONAM® 20, are believed to provide a viable alternative to antibiotics for controlling bacterial infections in fuel-ethanol fermentations.

Example 2

Lactobacilli MRS broth (25% strength) was prepared and dispensed in 10 ml amounts into test tubes and autoclaved for 20 minutes at 121° C. The biocides were added to the test tubes in the desired concentrations, and then 100 microliters of an overnight broth of *Lactobacillus fermentans* were added to the respective test tubes and incubated at 37° C. for 24 hours.

In this example, a synergistic effect was demonstrated by testing the combination of Nisin, designated as component A, and 2-bromo-2-nitropropane-1,3-diol, designated as component B in a series of tests in varying ratios and a range of concentrations against the bacterium, *Lactobacillus fermentans*, using the method described above. The results are shown below.

| Quantities producing endpoints (ppm) | | | | | | |
|---|---|---|---|---|---|---|
| $Q_a$ | $Q_A$ | $Q_b$ | $Q_B$ | $Q_A/Q_a$ | $Q_B/Q_b$ | $Q_A/Q_a + Q_B/Q_b$ |
| 1.0 | — | — | — | — | — | — |
|  | 0.1 |  | 25 | 0.1 | 0.5 | 0.6 |
|  | 0.25 |  | 25 | 0.25 | 0.5 | 0.75 |
|  | 0.25 |  | 10 | 0.25 | 0.2 | 0.45 |
|  | 0.5 |  | 10 | 0.5 | 0.2 | 0.7 |
| — | — | 50 | — | — | — | — |

Synergism was demonstrated by the method of described by Kull, E. C., Eisman, P. C., Sylwestrwicz, H. D., and Mayer, R. L. 1961, APPLIED MICROBIOLOGY, 9:538-541, wherein:

$Q_A/Q_a + Q_B/Q_b$ is less than 1.

$Q_a$=Concentration of Compound A in parts per million, acting alone, which produced an endpoint;

$Q_b$=Concentration of Compound B in parts per million, acting alone, which produced an endpoint;

$Q_A$=Concentration of Compound A in parts per million, in the mixture, which produced an endpoint;

$Q_B$=Concentration of Compound B in parts per million, in the mixture, which produced an endpoint.

When the sum of $Q_A/Q_a$ and $Q_B/Q_b$ is greater than one, antagonism is indicated and when the sum is equal to one, additivity is indicated. When the sum of this value is less than one, synergism exists.

In the table above, as can be seen, the combination of Nisin with 2-bromo-2-nitropropane-1,3-diol provided synergistic results for the various combinations. This effectiveness would be quite useful for controlling bacteria prior to and/or during fermentations that make ethanol.

Example 3

In this example, a synergistic effect was demonstrated by testing the combination of Nisin, designated as component A, and 2,2-dibromo-3-nitrilopropionamide, designated as component B in a series of tests in varying ratios and a range of concentrations against the bacterium, *Lactobacillus fermentans*, using the method described above. The results are set forth below.

| Quantities producing endpoints (ppm) | | | | | | |
|---|---|---|---|---|---|---|
| $Q_a$ | $Q_A$ | $Q_b$ | $Q_B$ | $Q_A/Q_a$ | $Q_B/Q_b$ | $Q_A/Q_a + Q_B/Q_b$ |
| 1.0 | — | — | — | — | — | — |
|  | 0.1 |  | 60 | 0.1 | 0.6 | 0.7 |
|  | 0.1 |  | 80 | 0.1 | 0.8 | 0.9 |
|  | 0.25 |  | 60 | 0.25 | 0.6 | 0.85 |
|  | 0.5 |  | 20 | 0.5 | 0.2 | 0.7 |
|  | 0.5 |  | 40 | 0.5 | 0.4 | 0.9 |
| — | — | 100 | — | — | — | — |

In the table above, as can be seen, the combination of Nisin with 2,2-dibromo-3-nitrilopropionamide provided synergistic results for the various combinations. This effectiveness would be quite useful for controlling bacteria prior to and/or during fermentations that make ethanol.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for producing ethanol by fermentation comprising:
   a) fermenting a fermentable mash in the presence of at least one nonoxidizing biocide that is a dihalonitrilopropionamide, at least one polycyclic antibacterial peptide, and yeast in a vessel to produce ethanol and a solids content, wherein said nonoxidizing biocide controls growth of bacteria in the mash without reducing yeast population, and wherein said nonoxidizing biocide and said polycyclic antibacterial peptide are synergistic with regard to biocidal control of at least one bacteria during and/or after fermentation to produce ethanol wherein said synergistic is defined as:

$Q_A/Q_a + Q_B/Q_b$ is less than 1, and $Q_a$=Concentration of Compound A in parts per million, acting alone, which produced an endpoint;
   $Q_b$=Concentration of Compound B in parts per million, acting alone, which produced an endpoint;
   $Q_A$=Concentration of Compound A in parts per million, in the mixture, which produced an endpoint;
   $Q_B$=Concentration of Compound B in parts per million, in the mixture, which produced an endpoint;
   b) distilling the fermented mash to separate at least a portion of the ethanol from said solids content; and
   c) obtaining a distillers dried grains product from said solid content.

2. The method of claim 1, wherein said distillers grains product contains less than 100 ppm of the nonoxidizing biocide.

3. The method of claim 1, wherein the fermented mash in step (b) contains no greater than 10 ppm antibiotic.

4. The method of claim 1, wherein said fermented mash in step b) has less than 10 ppm of nonoxidizing biocide present after distillation.

5. The method of claim 1, wherein said fermented mash in step b) has less than 1 ppm of nonoxidizing biocide present after distillation.

6. The method of claim 1, wherein the bacteria are *Lactobacillus* sp., *Acetobacter* sp., or combinations thereof.

7. The method of claim 1, wherein the bacteria are obligate anaerobes.

8. The method of claim 1, wherein the fermented mash in step (a) has at least 5-fold less lactic acid on a weight % basis than the same fermented mash fermented in the absence of the nonoxidizing biocide.

9. The method of claim 1, wherein the fermented mash in step (a) has at least 5-fold less acetic acid on a weight % basis than the same fermented mash fermented in the absence of the nonoxidizing biocide.

10. The method of claim 1, wherein the nonoxidizing biocide is 2,2-dibromo-3-nitrilopropionamide.

11. A method for producing ethanol with fermentation comprising:
   a) providing fermentable mash, at least one nonoxidizing biocide that is a dihalonitrilopropionamide, at least one polycyclic antibacterial peptide, and at least one yeast as a mixture in a vessel under conditions wherein fermentation of the mash occurs to produce ethanol and the at least one nonoxidizing biocide controls growth of bacteria in the mash without killing the yeast, and wherein said nonoxidizing biocide and said polycyclic antibacterial peptide are synergistic with regard to biocidal control of at least one bacteria during and/or after fermentation to produce ethanol wherein said synergistic is defined as:

$Q_A/Q_a + Q_B/Q_b$ is less than 1, and $Q_a$=Concentration of Compound A in parts per million, acting alone, which produced an endpoint;
   $Q_b$=Concentration of Compound B in parts per million, acting alone, which produced an endpoint;
   $Q_A$=Concentration of Compound A in parts per million, in the mixture, which produced an endpoint;
   $Q_B$=Concentration of Compound B in parts per million, in the mixture, which produced an endpoint;
   b) distilling the fermented mash to separate at least a portion of the ethanol from a solids content of the fermented mash, wherein said fermented mash has less than 1 ppm of nonoxidizing biocide and less than 10 ppm of antibiotic present after said distilling, and
   c) obtaining a distillers dried grains product from said solid content.

12. A composition comprising at least one nonoxidizing biocide and at least one polycyclic antibacterial peptide, wherein said nonoxidizing biocide is 2-bromo-2-nitropropane-1,3-diol or 2,2-dibromo-3-nitrilopropionamide or a halide analog thereof, and wherein said nonoxidizing biocide and said polycyclic antibacterial peptide are present in a synergistic amount with regard to controlling at least one bacteria during a fermentation to produce ethanol wherein said synergistic amount is defined as:

$Q_A/Q_a + Q_B/Q_b$ is less than 1, and $Q_a$=Concentration of Compound A in parts per million, acting alone, which produced an endpoint;
$Q_b$=Concentration of Compound B in parts per million, acting alone, which produced an endpoint;
$Q_A$=Concentration of Compound A in parts per million, in the mixture, which produced an endpoint;
$Q_B$=Concentration of Compound B in parts per million, in the mixture, which produced an endpoint.

13. The method of claim 1, wherein the nonoxidizing biocide present in the fermentable mash is provided by introducing process water containing nonoxidizing biocide into a fermentation vessel used for the fermenting.

14. The method of claim 1, wherein said dihalonitrilopropionamide is added to the fermentable mash in an amount of from 10 ppm to 500 ppm, and said polycyclic antibacterial peptide is added to the fermentable mash in an amount of from 0.01 ppm to 500 ppm.

15. The method of claim 1, wherein said dihalonitrilopropionamide is added to the fermentable mash in an amount of from 20 ppm to 80 ppm, and said polycyclic antibacterial peptide is added to the fermentable mash in an amount of from 0.1 ppm to 0.5 ppm.

16. The method of claim 1, wherein said dihalonitrilopropionamide is 2,2-dibromo-3-nitrilopropionamide and said polycyclic antibacterial peptide is Nisin.

17. The method of claim 11, wherein said dihalonitrilopropionamide is added to the fermentable mash in an amount of from 10 ppm to 500 ppm, and said polycyclic antibacterial peptide is added to the fermentable mash in an amount of from 0.01 ppm to 500 ppm.

18. The method of claim 11, wherein said dihalonitrilopropionamide is added to the fermentable mash in an amount of from 20 ppm to 80 ppm, and said polycyclic antibacterial peptide is added to the fermentable mash in an amount of from 0.1 ppm to 0.5 ppm.

19. The method of claim 11, wherein said dihalonitrilopropionamide is 2,2-dibromo-3-nitrilopropionamide and said polycyclic antibacterial peptide is Nisin.

20. The composition of claim 12, wherein said polycyclic antibacterial peptide and said nonoxidizing biocide are present in a weight ratio of polycyclic antibacterial peptide to nonoxidizing biocide of from 1:2 to 1:1000.

21. The composition of claim 12, wherein said polycyclic antibacterial peptide and said nonoxidizing biocide are present in a weight ratio of polycyclic antibacterial peptide to nonoxidizing biocide of from 1:20 to 1:1000.

22. The composition of claim 12, wherein said nonoxidizing biocide is 2-bromo-2-nitropropane-1,3-diol or 2,2-dibromo-3-nitrilopropionamide, and said polycyclic antibacterial peptide is Nisin.

* * * * *